(12) United States Patent
Davis et al.

(10) Patent No.: US 10,234,457 B2
(45) Date of Patent: Mar. 19, 2019

(54) ENZYME DETECTION DEVICE

(71) Applicant: Mologic Limited, Bedfordshire (GB)

(72) Inventors: Paul Davis, Sharnbrook (GB); Gita Parekh, Milton Keynes (GB)

(73) Assignee: Mologic Limited, Bedfordshire (GB)

( * ) Notice: Subject to any disclaimer, the term of this patent is extended or adjusted under 35 U.S.C. 154(b) by 846 days.

(21) Appl. No.: 14/395,777

(22) PCT Filed: Apr. 22, 2013

(86) PCT No.: PCT/GB2013/051007
§ 371 (c)(1),
(2) Date: Oct. 20, 2014

(87) PCT Pub. No.: WO2013/156794
PCT Pub. Date: Oct. 24, 2013

(65) Prior Publication Data
US 2015/0168407 A1    Jun. 18, 2015

(30) Foreign Application Priority Data

Apr. 20, 2012 (GB) .................................. 1206977.9

(51) Int. Cl.
*G01N 33/50* (2006.01)
*G01N 33/573* (2006.01)

(52) U.S. Cl.
CPC . *G01N 33/573* (2013.01); *G01N 2333/96419* (2013.01); *G01N 2333/96494* (2013.01)

(58) Field of Classification Search
None
See application file for complete search history.

(56) References Cited

U.S. PATENT DOCUMENTS

| | | | |
|---|---|---|---|
| 6,342,349 B1 * | 1/2002 | Virtanen | B01J 19/0046 435/6.11 |
| 7,097,983 B2 | 8/2006 | Markovsky et al. | |
| 8,592,167 B2 * | 11/2013 | Davis | C12Q 1/37 435/7.1 |
| 2006/0246599 A1 | 11/2006 | Rosenstein et al. | |

FOREIGN PATENT DOCUMENTS

| | | |
|---|---|---|
| CN | 101896292 A | 11/2010 |
| EP | 1 557 474 A1 | 7/2005 |
| GB | 2437311 A | 10/2007 |
| GB | 2452076 A | 2/2009 |
| KR | 2012-0026728 A | 3/2012 |
| WO | WO-2006/089027 A2 | 8/2006 |
| WO | WO-2009/063208 A2 | 5/2009 |

OTHER PUBLICATIONS

Jean, F., et al. "Detection of Endopeptidase Activity and Analysis of Cleavage Specificity Using a Radiometric Solid-Phase Enzymatic Assay," Analytical Biochemistry 194: 399-406 (1991).
International Search Report and Written Opinion for PCT/GB2013/051007 dated Jul. 9, 2013.
Search Report for GB1206977.9 dated Aug. 9, 2012.
Anamelechi et al., "Streptavidin binding and endothelial cell adhesion to biotinylated fibronectin," Langmuir, 23(25):12583-12588 (2007).
Doucet et al., "Broad coverage identification of multiple proteolytic cleavage site sequences in complex high molecular weight proteins using quantitative proteomics as a complement to edman sequencing," Mol Cell Proteomics, 10(5):M110.003533 (2011).
Dupont, D., et al., "A New Approach to Monitoring Proteolysis Phenomena Using Antibodies Specifically Directed Against the Enzyme Cleavage Site on its Substrate", Analytical Biochemistry 317 (2003) 240-246.
Gustafson, et al., "Synthesis and Characterization of a Matrix-Metalloproteinase Responsive Silk-Elastinlike Protein Polymer", Bio Macromolecules, 2013, 14, 618-625.
Hefle, S., et al., "Validated sandwich enzyme-linked immunosorbent assay for casein and its application retail and milk-allergic complaint foods", Abstract, Nov. 2, 2014.

* cited by examiner

*Primary Examiner* — Gary Counts
(74) *Attorney, Agent, or Firm* — Andrus Intellectiol Property Law, LLP

(57) ABSTRACT

Described herein is an enzyme detection device for use in the detection of enzyme activity in a test sample. Also provided are indicator molecules for use in the detection of enzyme activity, particularly enzyme cleavage activity, in a test sample, and to methods for detecting the presence of enzyme activity.

16 Claims, 9 Drawing Sheets

Specification includes a Sequence Listing.

| Component | Size | Position from datum point |
|---|---|---|
| Backing card (51) | 75mm | 0mm |
| Nitrocellulose membrane (52) | 25mm | 16mm |
| Conjugate pad (53) | 10mm | 7mm |
| Buffer pad (54) | 11mm | 0mm |
| Absorbent pad (57) | 23mm | 52mm |
| Double sided tape (55) | 5mm | 16mm |
| Sample pad/blood separator pad (56) | 7mm | 16mm |

| | Cut-off (ng/ml) |
|---|---|
| 1 CS | 250-500 |
| 2 CS | 125-250 |
| 3 CS | 250-500 |
| 5 CS | 31.25-62.5 |
| 7 CS | <31.25 |

ENZYME DETECTION DEVICE

This application is a 371 national stage application of PCT/GB2013/051007, filed Apr. 22, 2013, which claims priority to GB 1206977.9, filed Apr. 20, 2012. The entire contents of each of these applications are hereby incorporated by reference.

SEQUENCE LISTING

The instant application contains a Sequence Listing which has been submitted in ASCII format via EFS-Web and is hereby incorporated by reference in its entirety. Said ASCII copy, created on February 9, is named P109132US00_ST25.txt and is 4 KB in size.

FIELD OF THE INVENTION

The present invention relates to an enzyme detection device, particularly although not exclusively, a device for use in the detection of enzyme activity in a test sample. The invention also relates to indicator molecules for use in the detection of enzyme activity in a test sample and methods for detecting the presence of enzyme activity in a test sample.

BACKGROUND TO THE INVENTION

Enzymes constitute a family of proteins involved in catalysing chemical reactions within living organisms. As a result of their importance, there are numerous situations in which it is necessary and/or beneficial to measure enzyme levels, and importantly, enzyme activity.

In particular, increases in enzyme activity have been found to correlate with specific conditions and/or diseases. For example up-regulated protease activity has been associated with many aspects of cancer progression. The measurement of enzyme activity in samples taken from individuals with a particular condition or suspected of having a specific condition or disease may therefore be useful for prognostic or diagnostic purposes.

Within the enzyme family, there are six major categories of enzyme: —oxidoreductases; transferases; hydrolases; lyases; isomerases and ligases. This classification is based upon the type of reactions catalysed by the enzymes within each category. For example, hydrolases typically catalyse the hydrolysis of chemical bonds within their substrates, and include inter alia enzymes such as proteases, peptidases, lipases and nucleases.

Assays have previously been developed for the measurement of enzyme activity; however, these are often associated with problems or limitations. For example, some enzyme detection devices can only be used to measure the activity of enzymes that cleave their substrates. One such device is described in US2006/0003394 involving a kit comprising a substrate-reporter "reactive complex" that is added to a test sample known or suspected of containing the enzyme. The enzyme-reactive complex is applied to a chromatographic medium whereupon immobilisation of the reactive complex occurs at an upstream site. If the substrate is cleaved by any enzyme present within the test sample, the reporter portion of the reactive complex is released and flows to a downstream site where it can be detected separately. Since the detection of enzyme activity is based on measurement of a reporter 'leaving group' from the original reactive complex, this device is not at all suitable for measuring the activity of enzymes that modify, rather than cleave, their substrates. For example, transferases catalyse the transfer of a functional group, for example a phosphate group, to their substrates and thus could not be detected using the device described in US2006/0003394.

Different devices have been described that are suitable for detecting the activity of enzymes that modify their substrates. One such device is described in WO2009/024805, which relies on use of a "substrate recognition molecule" (SRM) carrying a detectable label, wherein the SRM specifically binds to the enzyme substrate in either the unmodified or modified state.

Assays such as that described in WO2009/024805, frequently require a very specific detection reagent suitable for discriminating between both modified and unmodified forms of an enzyme substrate and for effective detection. The accuracy and reliability of assay results obtained using such devices can therefore be limited by the availability of suitable reagents.

SUMMARY OF INVENTION

The present invention seeks to address at least some of the problems associated with existing enzyme detection devices by providing a standardised, robust device for the accurate detection of enzyme activity within a test sample.

In particular, the current invention provides a device wherein detection of enzyme activity is effectively conducted in two phases. In the first phase, reagents are used to discriminate between modified and unmodified forms of the enzyme substrate, and in the second phase, detection of one or other or both of these forms is measured in order to assess enzyme activity. The present device gives rise to a standardised assay format for measuring enzyme activity in a test sample, which can readily be adapted to measure the activity of any enzyme of interest.

The present invention also provides an indicator molecule for use in the detection of enzyme activity in a test sample.

In accordance with a first aspect of the invention, there is provided an indicator molecule for use in the detection of enzyme activity in a test sample comprising:
(i) an enzyme modifiable region, which can be modified by said enzyme causing transformation of the region from an unmodified to a modified state;
(ii) a separate capture site which can be bound by a capture molecule irrespective of the state of modification of the enzyme modifiable region; and
(iii) a separate detection site.

In certain embodiments, the enzyme modifiable region of the indicator molecule comprises a cleavage site such that the indicator molecule is used to detect the activity of enzymes capable of cleaving their substrates. Cleavage at the cleavage site causes the enzyme modifiable region to transform from an unmodified to a modified state, and also causes release of a fragment of the indicator molecule consisting of, consisting essentially of, or comprising the detection site. The enzyme or enzymes to be detected may be selected from the following categories: —oxidoreductases, hydrolases and lyases, and include the subcategories of protease, peptidase, lipase, nuclease, carbohydrase, phosphatise, sulphatase, neuraminidase, esterase, DNAse and RNAse. In preferred embodiments, the indicator molecule is used to detect protease activity.

In certain embodiments of the invention, the enzyme modifiable region may comprise multiple cleavage sites, wherein cleavage at any one of the sites causes the detection site to separate from the capture site of the indicator molecule. In the context of the present invention, the term 'multiple' means at least two, at least three, at least four, and so forth.

Thus, the present invention provides an indicator molecule for use in the detection of enzyme cleavage activity in a test sample comprising:
(i) an enzyme modifiable region comprising multiple cleavage sites, wherein cleavage at any one of the cleavage sites causes transformation of the region from an unmodified to a modified state;
(ii) a separate capture site which can be bound by a capture molecule irrespective of the state of modification of the enzyme modifiable region; and
(iii) a separate detection site.

In certain embodiments, the indicator molecule includes between 2, 3, 4, 5 and 10, 11, 12, 13, 14, 15, 16, 17, 18, 19, 20, 25, 50, 100, 500 or 1000 cleavage sites. In some embodiments, the indicator molecule includes between 2 and 5, 6, 7, 8, 9 or 10 cleavage sites.

In one embodiment, the multiple cleavage sites may all be identical. In this configuration, the repeated cleavage site may be relatively non-specific or may be highly specific for one enzyme or enzyme subtype as defined above. Moreover, use of an indicator molecule of this type may help to increase the sensitivity of the enzyme detection device by providing a means to increase the concentration of cleavage sites present within the test sample.

In other embodiments, the indicator molecule may comprise multiple cleavage sites wherein there are at least two different cleavage sites present within the same indicator molecule. In preferred embodiments of the invention, the indicator molecule may comprise at least three, at least four, at least five, and up to at least 8 different cleavage sites.

In a further preferred embodiment, the different cleavage sites are recognised by different enzymes or different categories, subcategories or subtypes of enzymes as defined above, such that the device of the invention can be used to detect the activity of multiple different enzymes. The activities may be grouped, such that the detection of enzyme activity gives a useful result. For example, a group of enzymes may be involved in a disease state such that detection of the relevant activity of one or more of the enzyme group is diagnostically useful.

Use of multiple cleavage sites (whether identical or non-identical) may be particularly useful for situations in which very low levels of enzyme activity are to be detected in a test sample. For example, an indicator molecule having multiple cleavage sites as defined above may be used to detect enzyme activity in a urine sample containing low levels of protease.

Once an indicator molecule according to the first aspect of the invention has been cleaved, the detection site may be detected using any suitable means known to those skilled in the art. In certain embodiments, the detection site itself may comprise a reporter moiety wherein a reporter moiety is defined herein as any moiety capable of signal generation or production. In a preferred embodiment of the invention, the reporter moiety is selected from the following: —a gold particle; a chromogen; a luminescent compound; a fluorescent molecule; a radioactive compound; a visible compound; a liposome or other vesicle containing signal producing substances; an electroactive species; or a combination of enzyme and its substrate. A suitable enzyme-substrate combination for use as a reporter moiety may be the enzyme alkaline phosphatase and the substrate nitro blue tetrazolium-5-bromo-4-chloro-3-indolyl phosphate. Alternatively, or in addition, the detection site may be bound by a separate reporter molecule as described herein below.

The indicator molecules as described herein may be used in conjunction with an enzyme detection device according to the present invention.

In accordance with a second aspect of the invention, there is provided an enzyme detection device for use in the detection of enzyme activity in a test sample comprising:
(i) an indicator molecule for adding to the test sample, said indicator molecule comprising
(a) an enzyme modifiable region, which can be modified by said enzyme causing transformation of the region from an unmodified to a modified state; and
(b) a detection region, which is not modified by the enzyme and can be bound by a reporter molecule irrespective of the state of modification of the enzyme modifiable region,
(ii) a selective capture zone to receive the test sample, wherein the selective capture zone comprises selective recognition molecules capable of binding to the enzyme modifiable region of the indicator molecule selectively in one or other of the modified or unmodified states; and
(iii) a detection zone to receive the test sample following contact of the test sample with the selective capture zone, wherein the detection zone is spatially separated from the selective capture zone such that exposure of the test sample to the detection zone occurs after prior exposure of the test sample to the selective capture zone and wherein only indicator molecules that do not bind to the selective recognition molecules in the selective capture zone pass into the detection zone and wherein the indicator molecule is detected at the selective capture zone and/or the detection zone.

In use, the test sample is first contacted with the selective capture zone, wherein either the modified or unmodified indicator molecule is captured by binding to the selective recognition molecules, and subsequently contacted with the detection zone wherein only indicator molecules that do not bind to the selective recognition molecules in the selective capture zone pass into the detection zone. Indicator molecules that are not captured in the selective capture zone may be detected using any suitable means known to those skilled in the art in the detection zone as described herein below.

The test sample for use in conjunction with the device of the invention may be any material known or suspected to contain an enzyme and may be derived from any source. In certain embodiments, the test sample may be derived from a biological source including fluids such as blood, saliva, urine, milk, fluid from a wound, ascites fluid, peritoneal fluid, amniotic fluid and so forth. In a preferred embodiment, the test sample is wound fluid and the device is used to detect enzyme activity, preferably protease activity, in the wound fluid as a means to assess the status and/or rate of healing of a wound. In a further preferred embodiment, the test sample is urine and the device is used to detect the activity of enzymes, in particular proteases, in the urine.

The test sample may be collected by any suitable means and presented in any form suitable for use with the present device including solid or liquid forms. Moreover, as part of obtaining the test sample from its original source, the sample may undergo one or more processing or pre-treatment steps prior to testing using the device of the invention. In one embodiment, a solid sample may be processed so as to produce a solution or suspension for testing. Moreover, in certain embodiments, the test sample may be stored, for example frozen at around −20° C. as a means of preserving the sample, for any given length of time prior to testing using the device of the invention.

The device of the invention is for detecting specifically enzyme activity in a test sample. The device may therefore be used to measure indirectly whether an enzyme is physically present or absent in any given test sample. Alternatively, a test sample may be provided in which an enzyme is known to be present, and the activity of said enzyme may be measured using the device of the invention. For example, test samples containing a known amount of enzyme and one or more modulators or suspected modulators of enzyme activity may be used in conjunction with the present device. In one embodiment of the invention, the device is used to test potential modulators or inhibitors of enzyme activity.

The present device relies on use of an indicator molecule which is added to the test sample. The indicator molecule comprises firstly an 'enzyme modifiable region' which is selected such that it acts as a substrate suitable for modification by the enzyme of interest to be detected. Modification of the enzyme modifiable region by the enzyme of interest, if present within the test sample, causes transformation of this region from an unmodified to a modified state.

In the context of the present invention, 'modification of the enzyme modifiable region' should be taken to mean any change to this substrate region that can be brought about by the action of any enzyme of interest. In certain embodiments of the invention, modification may include events such as cleavage of the enzyme modifiable region or the addition or elimination of a chemical group to or from this region, respectively. Moreover, the transformation from the unmodified to the modified state must be such that the two forms of the enzyme modifiable region are distinguishable by a selective recognition molecule of the device as described further below.

In preferred embodiments of the invention, the enzyme modifiable region of the indicator molecule comprises a peptide, a protein, a carbohydrate, a lipid or a nucleic acid. Moreover, the enzyme to be detected using the device of the invention may be selected from the following categories: oxidoreductases, transferases, hydrolases, lyases, isomerases and ligases, including the subcategories of protease; peptidase; lipase; nuclease; carbohydrase; phosphatase; sulphatase; neuraminidase; esterase; DNAse; RNAse; kinase; glycosyl transferase; oxidase; reductase; and transaminase.

In preferred embodiments, the device of the invention is used to detect enzyme activity in fluids derived from wounds. In such embodiments, the enzymes to be detected are preferably proteases, and in particular matrix metalloproteases (MMPs) and human neutrophil-derived elastase (HNE). In a preferred embodiment, the enzyme to be detected is a cathepsin, in particular cathepsin G.

In further preferred embodiments, the device of the invention is used to detect enzyme activity in a urine sample collected from a subject. In such embodiments, the enzymes to be detected are preferably proteases and in particular, matrix metalloproteases (MMPs) and human neutrophil elastase (HNE).

In certain embodiments, the enzyme modifiable region of the indicator molecule may comprise or consist of a region which is identical to the enzyme's natural substrate or a fragment thereof. In other embodiments, the enzyme modifiable region may be engineered such that it comprises a non-native enzyme substrate. For example, the enzyme modifiable region may be engineered or mutated such that the rate and/or specificity of enzyme activity is increased (or decreased as appropriate) relative to the rate and/or specificity of activity exhibited by the enzyme of interest against its natural substrate.

Furthermore, the enzyme modifiable region may be selected such that it is relatively non-specific meaning that it is capable of being recognised or acted on by more than one enzyme or sub-category of enzyme as defined above. For example, an enzyme modifiable region comprising or consisting of a peptide substrate may be subject to cleavage by both proteases and peptidases, or a subset of proteases and/or peptidases. In circumstances wherein the enzyme modifiable region is recognised or acted on by more than one enzyme, the device may be used to detect the presence in a test sample of any of such enzymes (for example a particular group or category of enzyme) capable of modifying the indicator molecule.

Alternatively, the enzyme modifiable region may be selected such that is highly specific meaning that only one enzyme or one sub-type of enzyme is capable of recognising and modifying this region. In this context, a sub-type is defined as a sub-classification of enzymes falling within any of the sub-categories defined above. In such embodiments, the device may be tailored to the detection of a single enzyme or single enzyme sub-type within a test sample.

In certain embodiments, the enzyme modifiable region may contain only a single modification site i.e. a single site or position at which an enzyme can act. For example, the enzyme modifiable region may contain a single cleavage site recognised by one or more protease enzymes. Modification at this particular site or position is thus responsible for transforming the enzyme modifiable region from its unmodified to modified state. Alternatively, the enzyme modifiable region may contain multiple modification sites such that modification at any one (or more) of these sites results in transformation of the region from an unmodified to a modified state. In the context of the present invention, the term 'multiple' means at least two, at least three, at least four and so forth. For example, the enzyme modifiable region may contain multiple phosphorylation sites recognised by one or more kinase enzymes.

In certain embodiments, the indicator molecule includes between 2, 3, 4, 5 and 10, 11, 12, 13, 14, 15, 25, 50, 100, 500 or 1000 modification sites. In some embodiments, the indicator molecule includes between 2 and 5, 6, 7, 8, 9 or 10 modification sites.

Wherein multiple modification sites exist within the enzyme modifiable region, these sites may all be identical. For example, the enzyme modifiable region may contain multiple identical cleavage sites. The repeated cleavage site may be relatively non-specific or may be highly specific for one enzyme or enzyme sub-type as defined above.

In other embodiments, the enzyme modifiable region may comprise multiple modification sites wherein there are at least two different modification sites present within the same indicator molecule. In preferred embodiments of the invention, the indicator molecule may comprise at least three, at least four, at least five, and up to at least fifty different modification sites. Modification at any one of these sites may lead to transformation of the region from an unmodified to a modified state. In a further preferred embodiment, the different modification sites are recognised by different enzymes or different categories, sub-categories or sub-types of enzymes as defined above, such that the device of the invention can be used to detect the activity of multiple different enzymes within a test sample.

Use of multiple modification sites (whether identical or non-identical) within an indicator molecule may help to increase the sensitivity of the enzyme detection device by providing a means to increase the concentration of modification sites present within the test sample. This may be particularly useful for situations in which very low levels of enzyme activity are to be detected in a test sample. For example, an indicator molecule having multiple modification sites as defined above may be used to detect enzyme activity in a urine sample containing low levels of protein.

In addition to an enzyme modifiable region, the indicator molecule of the present invention comprises a detection region which is not subject to any modification by the enzyme to be detected. The detection region of the indicator molecule may be attached to the enzyme modifiable region by any suitable means. In one embodiment, attachment is via a direct covalent linkage. In an alternative embodiment, the detection region of the indicator molecule is attached to the enzyme modifiable region via a linker or carrier protein. In a preferred embodiment of the indicator molecule, the detection region and the enzyme modifiable region consist of different peptides, and the carrier protein consists of bovine serum albumin. For embodiments wherein the enzyme modifiable region and detection region are associated via a carrier protein, the indicator molecule may include multiple enzyme modifiable regions and/or detection regions.

In a further preferred embodiment of the invention, the detection region of the indicator molecule comprises a capture site and the detection zone of the device comprises capture molecules to which the capture site of the indicator molecule, if present, can bind. In a further preferred embodiment, the detection region of the indicator molecule comprises a detection site separate from the capture site.

Thus, in a third aspect of the invention, there is provided an indicator molecule for use in the detection of enzyme activity in a test sample comprising:
(i) an enzyme modifiable region, which can be modified by said enzyme causing transformation of the region from an unmodified to a modified state, the unmodified and modified states being structurally distinguishable in terms of binding by a selective recognition molecule;
(ii) a separate capture site which can be bound by a capture molecule irrespective of the state of modification of the enzyme modifiable region; and
(iii) a separate detection site which can be bound by a reporter molecule irrespective of the state of modification of the enzyme modifiable region and irrespective of prior or simultaneous binding of the capture molecule to the capture site.

An indicator molecule according to the third aspect of the invention may be used to detect enzyme activity in conjunction with the enzyme detection device described herein, or may be used in the context of other enzyme detection assays. All embodiments described in respect of the indicator molecule, as used in conjunction with the enzyme detection device described herein are equally applicable to the indicator molecule of the third aspect of the invention.

In certain embodiments, the enzyme modifiable region of the indicator molecule comprises one or more cleavage sites, such that the indicator molecule can be used to detect the activity of enzymes capable of cleaving their substrates. The enzyme or enzymes to be detected may be selected from the following categories: —oxidoreductases, hydrolases and lyases, and include the subcategories of protease, peptidase, lipase, nuclease, carbohydrase, phosphatise, sulphatase, neuraminidase, esterase, DNAse and RNAse. In preferred embodiments, the indicator molecule is used to detect protease activity.

In certain embodiments of the invention, the enzyme modifiable region may comprise multiple cleavage sites, wherein cleavage at any one of the sites causes the detection site to separate from the capture site of the indicator molecule. In the context of the present invention, the term 'multiple' means at least two, at least three, at least four, and so forth.

In certain embodiments, the indicator molecule includes between 2, 3, 4, 5 and 10, 11, 12, 13, 14, 15, 16, 17, 18, 19, 20, 25, 50, 100, 500 or 1000 cleavage sites. In some embodiments, the indicator molecule includes between 2 and 5, 6, 7, 8, 9 or 10 cleavage sites.

In one embodiment, the multiple cleavage sites may all be identical. In this configuration, the repeated cleavage site may be relatively non-specific or may be highly specific for one enzyme or enzyme subtype as defined above. Moreover, use of an indicator molecule of this type may help to increase the sensitivity of the enzyme detection device by providing a means to increase the concentration of cleavage sites present within the test sample.

In other embodiments, the indicator molecule may comprise multiple cleavage sites wherein there are at least two different cleavage sites present within the same indicator molecule. In preferred embodiments of the invention, the indicator molecule may comprise at least three, at least four, at least five, and up to at least 8 different cleavage sites.

In a further preferred embodiment, the different cleavage sites are recognised by different enzymes or different categories, subcategories or subtypes of enzymes as defined above, such that the device of the invention can be used to detect the activity of multiple different enzymes. The activities may be grouped, such that the detection of enzyme activity gives a useful result. For example, a group of enzymes may be involved in a disease state such that detection of the relevant activity of one or more of the enzyme group is diagnostically useful.

Use of multiple cleavage sites (whether identical or non-identical) may be particularly useful for situations in which very low levels of enzyme activity are to be detected in a test sample. For example, an indicator molecule having multiple cleavage sites as defined above may be used to detect enzyme activity in a urine sample containing low levels of protease.

Once an indicator molecule according to the third aspect of the invention has been cleaved, the detection site may be detected using any suitable means known to those skilled in the art. In certain embodiments, the detection site itself may comprise a reporter moiety wherein a reporter moiety is defined herein as any moiety capable of signal generation or production. In a preferred embodiment of the invention, the reporter moiety is selected from the following: —a gold particle; a chromogen; a luminescent compound; a fluorescent molecule; a radioactive compound; a visible compound; a liposome or other vesicle containing signal producing substances; an electroactive species; or a combination of enzyme and its substrate. A suitable enzyme-substrate combination for use as a reporter moiety may be the enzyme alkaline phosphatase and the substrate nitro blue tetrazolium-5-bromo-4-chloro-3-indolyl phosphate.

In addition to an indicator molecule, the device of the invention comprises a selective capture zone comprising selective recognition molecules capable of binding to the enzyme modifiable region of the indicator molecule selectively in one or other of the modified or unmodified states. The selective recognition molecule is therefore the component of the present device capable of structurally distinguishing between the modified and unmodified forms of the indicator molecule, and thus facilitating separation of these two forms.

The selective recognition molecule may be such that it recognises only the unmodified form of the indicator molecule. Alternatively, the selective recognition molecule may be selected such it recognises only the modified form of the indicator molecule. In embodiments wherein the selective recognition molecule recognises the modified form of the indicator molecule and modification by the enzyme to be detected results in indicator molecule cleavage or fragmentation in any way, it is a requirement of the present device that the selective recognition molecule bind at least the fragment of the indicator molecule comprising the detection region.

In circumstances wherein the enzyme modifiable region of the indicator molecule comprises multiple modification sites, the selective capture zone of the device may contain different selective recognition molecules, each one capable of recognising at least one of the modified or unmodified forms adopted by the enzyme modifiable region. Wherein the selective capture zone of the device contains different selective recognition molecules, each tailored to discriminate between modified and unmodified forms of the enzyme modifiable region in respect of a particular modification at a particular site, it is preferable for the functioning of the device that the different selective recognition molecules all recognise either modified or unmodified forms of the indicator molecule.

The selective recognition molecule may be any molecule capable of structurally distinguishing between modified and unmodified forms of the enzyme modifiable region of the indicator molecule. In a preferred embodiment of the invention, the selective recognition molecule is an antibody or antigen binding fragment thereof, avidin, streptavidin or a derivative thereof, a lectin, a nucleic acid molecule, a receptor molecule, or a hormone binding protein. In a particularly preferred embodiment, the selective recognition molecule is an antibody capable of selectively recognising only the modified or unmodified form of the enzyme modifiable region. In the context of the present invention, the term antibody covers native immunoglobulins from any species, chimeric antibodies, humanised antibodies, $F(ab')_2$ fragments, Fab fragments, Fv fragments, sFv fragments and highly related molecules such as those based upon antibody domains which retain specific binding affinity (for example, single domain antibodies).

The primary role of the selective recognition molecule is to bind and thereby retain one or other of the unmodified or modified forms of the indicator molecule in the selective capture zone of the device thus allowing indicator molecules adopting the opposite form to pass into the detection zone. In a preferred embodiment, the selective capture zone comprises a solid phase support and the selective recognition molecule to which the indicator molecule binds selectively in one or other of the unmodified or modified states is located on or within the solid phase support.

It is preferable within the context of the present invention for the indicator molecules to bind to the selective recognition molecules with relatively high affinity. In preferred embodiments, the dissociation rate $(k_d)$ for the indicator molecule will be relatively low and preferably between 0M and $1 \times 10^{-7}$M (depending on the sensitivity required of the assay). In a particularly preferred embodiment of the invention, the dissociation rate for the indicator molecule will be between $1 \times 10^{-15}$M and $1 \times 10^{-9}$M. In particular, it is preferable for the selective recognition molecule to have a lower dissociation rate $(k_d)$ and a higher association rate $(k_a)$ for the indicator molecule than the enzyme to be detected has for the indicator molecule.

In a further preferred embodiment, the enzyme modifiable region cannot be modified or further modified by any enzyme once the indicator molecule is bound by a selective recognition molecule. This is particularly relevant and advantageous in circumstances wherein the selective recognition molecule selectively binds to the unmodified form of the indicator molecule.

Following contact of the test sample containing the indicator molecule with the selective capture zone of the device, the test sample is exposed to the detection zone of the device. Any indicator molecule not retained within the selective capture zone by virtue of binding to the selective recognition molecules located therein will be transferred to the detection zone.

In circumstances wherein the detection region of the indicator molecule comprises a capture site, the detection zone may comprise capture molecules capable of binding to the capture site of any indicator molecules present in the detection zone. In certain embodiments of the invention, such a binding interaction may be achieved as a result of direct binding of the capture site of the indicator molecule to the capture molecule present in the detection zone. In this context, direct binding means binding of the indicator molecule to the capture molecule without any intermediary.

In a preferred embodiment of the invention, the capture site of the indicator molecule and the capture molecule present in the detection zone of the device are two halves of a binding pair. In this context, a binding pair consists of two molecules or entities capable of binding to each other. In a preferred embodiment of the invention, the binding interaction is specific such that each member of the binding pair is only able to bind its respective partner, or a limited number of binding partners. It is preferable for the binding pair to exhibit relatively high affinity. This binding pair may be a binding pair found in nature or an artificially generated pair of interacting molecules or entities.

In a further preferred embodiment of the invention, the capture site of the indicator molecule and the capture molecule are two halves of a binding pair wherein the binding pair is selected from the following: —an antigen and an antibody or antigen binding fragment thereof; biotin and avidin, streptavidin, neutravidin or captavidin; an immunoglobulin or appropriate domain thereof and protein A or G; a carbohydrate and a lectin; complementary nucleotide sequences; a ligand and a receptor molecule; a hormone and hormone binding protein; an enzyme cofactor and an enzyme; an enzyme inhibitor and an enzyme; a cellulose binding domain and cellulose fibres; immobilised aminophenyl boronic acid and cis-diol bearing molecules; and xyloglucan and cellulose fibres and analogues, derivatives and fragments thereof.

In a particularly preferred embodiment of the device of the invention, the binding pair consists of biotin and streptavidin. In a further particularly preferred embodiment of the invention, the capture site of the indicator molecule comprises an epitope and the capture molecule within the detection zone comprises an antibody that specifically binds to the epitope present at the capture site.

In certain embodiments of the invention, binding of the capture site of the indicator molecule to the capture molecule within the detection zone of the device may be indirect. In the context of the present invention, "indirect binding" means binding mediated by some intermediate entity capable of bridging the indicator molecule and the capture molecule, for example an "adaptor" capable of simultaneously binding the capture site of the indicator molecule and the capture molecule.

Wherein binding of the indicator molecule to the capture molecule is indirect and mediated by an adaptor, it may be possible for a plurality of indicator molecules to bind to each capture molecule. In this context, a plurality means at least two, at least three, at least four, and so forth. This may be achieved by the incorporation of a multivalent adaptor molecule, for example, a streptavidin molecule capable of simultaneous binding to multiple biotin-containing indicator molecules and a biotin-containing capture molecule.

The detection region of the indicator molecule may be any substance or moiety suitable for detection by any means known to those skilled in the art. In one embodiment of the invention, the detection region itself may comprise a reporter moiety wherein a reporter moiety is defined herein as any moiety capable of signal generation or production. In a preferred embodiment of the invention, the reporter moiety is selected from the following: —a gold particle; a chromogen; a luminescent compound; a fluorescent molecule; a radioactive compound; a visible compound; a liposome or other vesicle containing signal producing substances; an electroactive species; or a combination of enzyme and its substrate. A suitable enzyme-substrate combination for use as a reporter moiety may be the enzyme alkaline phosphatase and the substrate nitro blue tetrazolium-5-bromo-4-chloro-3-indolyl phosphate. In a particularly preferred embodiment of the invention, the reporter moiety is a gold particle.

Alternatively or in addition to the above embodiments, the device may comprise one or more reporter molecule(s) bound or capable of binding to the detection region of the indicator molecule, and detection may be carried out using the signal generated by the reporter molecule(s). Binding of any reporter molecules to the detection region of the indicator molecule occurs irrespective of the state of modification of the enzyme modifiable region.

As described above, the reporter molecule may bind to the detection region of the indicator molecule at a specific "detection site", which is distinct and spatially separated from the capture site present within the detection region. The detection site may comprise a group of residues positioned directly adjacent or in close proximity to the capture site. Alternatively, the detection site may comprise a discrete portion of the indicator molecule spatially separated from the capture site, for example by virtue of a linker or spacer region or a carrier protein.

In embodiments of the device wherein the capture site of the indicator molecule binds directly to the capture molecules in the detection zone, it may be advantageous for the detection site to be distinct and/or spatially separated from the capture site so as not to impede simultaneous binding of the capture molecule and the reporter molecule to the indicator molecule.

Furthermore, despite the fact that the detection site and capture site are, in some cases, both defined as present within the "detection region" of the indicator molecule, these two sites may comprise or consist of different chemical entities conjoined so as to form the detection region of the molecule. For example, the capture site may comprise a first peptide antigen whilst the detection site may comprise a biotin moiety. In a preferred embodiment of the invention, the detection site comprises an epitope, distinct from any epitope present within the capture site, and the reporter molecule comprises an antibody which specifically binds to said epitope.

In certain other embodiments of the invention, the detection region may not have a separate detection site and the reporter molecule may bind to the detection region of the indicator molecule via the capture site provided that binding of the reporter molecule to the capture site does not impair the ability of the capture site to bind capture molecules in the detection zone. In a preferred embodiment of the invention, the capture site is biotin and the reporter molecule comprises a moiety capable of binding biotin, for example, an anti-biotin antibody or streptavidin or a derivative thereof.

The reporter molecule of the invention may comprise any reporter moiety capable of generating a signal for detection purposes. In preferred embodiments of the invention, the reporter moiety is selected from the following: —a gold particle; a chromogen; a luminescent compound; a fluorescent molecule; a radioactive compound; a visible compound; a liposome or other vesicle containing signal producing substances; an electroactive species; or a combination of enzyme and its substrate.

Moreover, binding of the reporter molecule to the indicator molecule may be indirect and mediated by an adaptor capable of simultaneously binding the detection region and the reporter molecule. In embodiments of the invention wherein the reporter molecule binds to the indicator molecule by virtue of an adaptor molecule, the adaptor may be pre-complexed with the detection region prior to the addition of the test sample to the indicator molecule.

The adaptor may be any material or molecule capable of mediating the indirect interaction of the detection region of the indicator molecule with the reporter molecule. In a preferred embodiment, the adaptor is streptavidin and the detection region comprises biotin. The adaptor may also be an "adaptor binding pair" wherein said binding pair comprises:

(i) a first member capable of binding to the detection region of the indicator molecule; and
(ii) a second member capable of binding to the first member of the pair and to the reporter molecule. In a particularly preferred embodiment of the invention, the detection region of the indicator molecule comprises biotin, the first member of the adaptor binding pair is avidin or streptavidin, the second member of the adaptor binding pair is biotin, and the reporter molecule comprises a moiety capable of binding biotin.

The inclusion of an adaptor molecule or an adaptor binding pair may facilitate the binding of multiple reporter molecules to each indicator molecule. For example, the use of multivalent streptavidin as the adaptor will allow for simultaneous binding of both a biotin-containing indicator molecule in addition to multiple biotin-containing reporter molecules.

In embodiments of the device wherein the reporter molecule is bound to the detection region of the indicator molecule via an adaptor or adaptor binding pair, this same adaptor or adaptor binding pair may serve to mediate indirect binding of the capture site to the capture molecules present in the detection zone of the device.

In preferred embodiments, the capture site of the indicator molecule comprises biotin and binds an adaptor comprising streptavidin. The streptavidin adaptor mediates binding to both biotin-containing reporter molecules and capture molecules also comprising biotin. Thus, the same adaptor exhibits three-way binding to link the detection region of the indicator molecule to both the reporter molecule and the capture molecule in the detection zone of the device.

In order for the device to function as intended, the selective capture zone must be spatially separated from the detection zone. This spatial separation must be such that it allows the test sample combined with the indicator molecule to first be brought into contact with the selective recognition molecules within the selective capture zone, and subsequently transferred to the detection zone of the device. In one embodiment, both the selective capture zone and detection zone are defined by separate solid phase supports and the selective recognition molecules and capture molecules, if present, are located on or within their respective solid phase support.

In a preferred embodiment of the invention, the device is configured as a flow device and the selective capture zone and detection zone are present at sequential locations along a chromatographic medium. The chromatographic medium may be mounted on a solid support. In a particularly preferred embodiment of the invention, the device is configured as a lateral flow device but may also be configured as a vertical flow device for example. The device may take the form of a test strip in certain embodiments.

The selective capture zone may be defined by the immobilization therein or thereon of selective recognition molecules capable of binding to the indicator molecule in one or other of the modified or unmodified states. The detection zone may be defined by the immobilization therein or thereon of capture molecules capable of binding to any indicator molecule left in the test sample following prior exposure of the test sample to the selective recognition molecules in the selective capture zone. Immobilization of selective recognition molecules and/or capture molecules may be achieved by any suitable means. Wherein the device is a flow device comprising a chromatographic medium, the selective recognition molecules and/or capture molecules may be immobilized by directly binding to the medium or immobilized indirectly via binding to a carrier molecule, such as a protein, associated with the medium.

The test sample may be applied to the chromatographic medium at a site upstream from the selective capture zone such that it is drawn, for example by capillary action, through the selective capture zone followed by the detection zone. The chromatographic medium may be made from any material through which a fluid is capable of passing, such as a fluidic channel or porous membrane. In a preferred embodiment of the invention, the chromatographic medium comprises a nitrocellulose strip or membrane. Thus, the device of the invention may include a sample application zone. The sample application zone may be separate from or may, in other embodiments, include the selective capture zone.

Wherein the device of the invention comprises reporter molecules capable of binding to the detection region of the indicator molecule, as described above, the device may additionally comprise a control capture zone comprising control capture molecules. The control capture zone is spatially separated from the selective capture zone and the detection zone.

In certain embodiments, the control capture molecules within the control capture zone may bind any reporter molecules that are not bound to indicator molecules. In preferred embodiments, the control capture molecules are antibodies capable of recognising an epitope within the reporter molecule, wherein the epitope is distinct from any epitope found within the indicator molecule. Detection of reporter molecule binding to the control capture molecules within the control capture zone may be used to determine the existence of functional reporter molecules within the device.

In further embodiments of the invention, the device may comprise, in addition to a reporter molecule, one or more "control reporter molecule(s)". Typically, the control reporter molecule(s) will comprise the same reporter moiety as the reporter molecule, but will not bind to the detection region of the indicator molecule. Such control reporter molecule(s) may be used to indirectly assess the presence and/or functioning of the reporter molecule within the device. Under these circumstances, the device may also comprise a control capture zone, spatially separated from the selective capture zone and the detection zone, comprising control capture molecules, wherein said control capture molecules are capable of binding the control reporter molecule, if present. In preferred embodiments, the control capture molecules are antibodies capable of recognising an epitope within the control reporter molecule, wherein the epitope is distinct from any epitope found within the indicator molecule or reporter molecule. Detection of control reporter molecule binding to the control capture molecules within the control capture zone may be used to indirectly assess the existence of functional reporter molecules within the device.

Wherein the device of the invention is configured as a flow device comprising a chromatographic medium, the selective capture zone, detection zone and control capture zone (if present) may be contained within a plastic housing, provided with means by which reporter molecules immobilised at one or more of the different zones can be detected. For example, the plastic housing may contain windows permitting visual inspection of the signal generated by reporter molecules bound at the one or more of the selective capture zone, detection zone and control capture zone. In certain embodiments, particularly embodiments wherein the selective recognition molecules bind to the unmodified form of the indicator molecule, the plastic housing may hide the selective capture zone from view such that only reporter molecules bound at the detection zone can be detected. This has the advantage that the end user sees a positive test line only in the presence of enzyme (at the detection zone).

In accordance with a further aspect of the invention, there is provided herein a method for detecting the presence of enzyme activity in a test sample, the method comprising the steps of:

(i) providing an enzyme detection device comprising
an indicator molecule for adding to the test sample, said indicator molecule comprising
  (a) an enzyme modifiable region, which can be modified by said enzyme causing transformation of the region from an unmodified to a modified state; and
  (b) a detection region, which is not modified by the enzyme and can be bound by a reporter molecule irrespective of the state of modification of the enzyme modifiable region;
a selective capture zone to receive the test sample, wherein the selective capture zone comprises selective recognition molecules capable of binding to the enzyme modifiable region of the indicator molecule selectively in one or other of the modified or unmodified states; and
a detection zone to receive the test sample following contact of the test sample with the first capture zone, wherein the detection zone is spatially separated from the first capture zone,
(ii) providing a test sample suspected of containing the enzyme activity;
(iii) adding the indicator molecules of the device to the test sample under conditions in which the enzyme activity, if present, can modify the enzyme modifiable region;
(iv) bringing the test sample into contact with the selective capture zone of the device such that indicator molecules in one or other of the modified or unmodified states are bound to the selective recognition molecules thereby allowing separation of either the modified or unmodified form of the indicator molecule from any indicator molecule in the opposite state, if present;

(v) bringing the test sample into contact with the detection zone wherein only indicator molecules that do not bind to the selective recognition molecules in the selective capture zone pass into the detection zone; and (vi) detecting any indicator molecule present within the selective capture zone and/or detection zone.

The method detailed above involves use of an enzyme detection device of the invention as described in detail elsewhere herein. All embodiments described in respect of the enzyme detection device and indicator molecule of the invention apply mutatis mutandis to these aspects of the methods of the invention and therefore are not repeated for reasons of conciseness.

The method of the invention requires addition of the indicator molecules of the device to the test sample under conditions in which the enzyme, if present (and active), can modify the enzyme modifiable region. The conditions used for carrying out the method may depend on the enzyme(s) of interest to be detected and may include variations in parameters such as time of incubation of the indicator molecule and test sample, temperature, pH. Furthermore, the conditions may be adjusted so as to influence the sensitivity of the assay; for example, a longer incubation time may increase the proportion of modified indicator molecules in the test sample.

The device and methods of the invention may be utilised in order to optimise assay conditions for an enzyme of interest in certain embodiments.

The amount or concentration of indicator molecules added to the test sample may also be varied depending on the enzyme(s) to be detected. It is preferable for sufficient indicator molecules to be added to the test sample such that the enzyme substrate is present in excess.

In certain embodiments of the invention, it may be preferable to incubate the indicator molecule with the test sample prior to bringing the test sample into contact with the selective capture zone of the device. This is particularly the case for embodiments wherein the selective recognition molecules present within the selective capture zone recognise the unmodified form of the indicator molecule and enzyme modifiable region cannot be modified by the enzyme once the indicator molecule is bound by a selective recognition molecule.

The results obtained by carrying out the present method will also be affected by the relationship between the quantity of selective recognition molecules present within the selective capture zone of the device and the quantity of indicator molecules added to the test sample. In certain embodiments of the invention, there are sufficient selective recognition molecules present so as to capture the total quantity of indicator molecules in the test sample in the selective capture zone should all the indicator molecules remain in the form recognised by the selective recognition molecules. The quantity of selective recognition molecules required to capture all the indicator molecules, or the quantity of indicator molecules that will saturate all the selective recognition molecule binding sites within the selective capture zone of the device can readily be determined experimentally by one skilled in the art.

If there are fewer selective recognition molecules than needed to capture all the indicator molecules in one or other state, particularly in circumstances wherein the selective recognition molecule binds to the unmodified form of the enzyme modifiable region, any unbound indicator molecules present in the selective capture zone may subsequently be transferred into the detection zone. The presence of indicator molecules in the detection zone of the device, wherein such indicator molecules should have been retained in the selective capture zone, may give rise to false positive results if detected within this zone. However, depending on the degree of assay sensitivity required, some degree of "leakage" of unbound indicator molecules into the detection zone wherein such indicator molecules should have been retained in the selective capture zone by virtue of their unmodified/modified state may be tolerable. Moreover, this "leakage" may be measured and taken into account by virtue of an appropriate control reaction.

As detailed above, the role of the selective recognition molecules is primarily to retain selectively either the unmodified or modified form of the indicator molecule within the selective capture zone of the device. Thus, in order to retain the indicator molecules within this zone, the selective recognition molecules must be localised within the selective capture zone such that they are not transferred to the detection zone together with the test sample. Localisation may be achieved via attachment of the selective recognition molecules to a solid support. In a preferred embodiment of the invention, the device is a flow device and the selective recognition molecules are immobilized at a discrete location along the long axis of a chromatographic medium. Immobilization of the selective recognition molecules may be achieved by any suitable means available to one of skill in the art.

After the test sample has been brought into contact with the selective capture zone, and indicator molecules in one or other of modified or unmodified form have bound to the selective recognition molecules therein, the test sample is then transferred to the detection zone. If the device is configured such that the selective recognition molecules bind to the unmodified form of the enzyme modifiable region, any modified forms of the indicator molecule will be transferred to the detection zone. If the device is configured such that the selective recognition molecules bind selectively to the modified form of the enzyme modifiable region, unmodified indicator molecule will be transferred to the detection zone.

Depending on the configuration of the device and the read-out desired by the end-user, the method of the invention may involve detecting the presence and/or level of indicator molecule within the selective capture zone or within the detection zone or within both these zones. For example, if the device is such that the selective recognition molecules bind to unmodified forms of the indicator molecule, the presence of modified indicator molecules, if any, within the detection zone will indicate the presence of enzyme activity within the test sample. Alternatively, if the selective recognition molecules of the device bind to modified forms of the indicator molecule, the presence of modified indicator molecules, if any, within the selective capture zone will indicate the presence of enzyme activity within the test sample. In certain embodiments, it may be useful to measure the relative amount of indicator molecule bound within the selective capture zone as compared with the detection zone. In view of the existence of indicator molecule at one or other of these sites, an inverse relationship may typically exist between the signal generated at the selective capture zone and signal generated at the detection zone.

The methods as described above may be used to determine whether enzyme activity is present or absent in any given test sample. The method may also be used in order to determine the relative amounts of enzyme activity in test samples based upon a comparison of two or more samples. In order to perform such a comparative analysis, the results obtained by carrying out the method of the invention using a first sample are compared with the results obtained by repeating the method using one or more additional test samples.

For example, in embodiments of the invention wherein the selective recognition molecules bind to unmodified forms of the indicator molecule, the signal intensity generated by modified indicator molecules present at the detection zone may be directly proportional to the level of enzyme activity in the test sample. Thus, a comparison of the signal intensity generated at the detection zone for each of two or more test samples may be used to calculate the relative level of enzyme activity in each sample.

Moreover, the ratio of signal intensities calculated from indicator molecule present at both the selective capture zone and detection zone may be directly proportional to the level of enzyme activity. Thus, a comparison of these ratio values for two or more samples may be used to determine the relative amount of enzyme in each sample.

This comparative analysis employing the method of the invention may be used for a variety of purposes. Firstly, measuring the relative levels of enzyme activity between two samples or more may be used as an indirect measure of the relative amount of total enzyme present within the different samples. Related to this, the present method may be first carried out in respect of a series of test samples containing known quantities of enzyme. The results obtained may be used to generate a standard curve of enzyme activity plotted against enzyme concentration. A further test sample containing an unknown quantity of enzyme may thereafter be tested for enzyme activity and, based on data available from the standard curve, the absolute amount of enzyme within the test sample may be determined.

In a further application of the current method, a comparison of the relative enzyme activity between two samples, for example a control sample and an experimental sample, may be used to assess the effect of a potential modulator or inhibitor on enzyme activity.

Detection of the presence of indicator molecule at the selective capture zone, the detection zone or both may be carried out by any means available to one of skill in the art. As detailed above, detection of the indicator molecule may be carried out by the detection of a reporter moiety present within the detection region.

In preferred embodiments of the invention, detection of the presence of the indicator molecule is carried out by the addition of a reporter molecule capable of binding to the detection region. Said reporter molecule may take any of the forms already described above and may associate with the detection region of the indicator molecule in any of the ways already detailed herein.

In a preferred embodiment of the invention, detection of the presence of indicator molecule is carried out by immunoassay using a reporter molecule containing an antibody capable of binding the detection region of the indicator molecule. In a particularly preferred embodiment, detection of the indicator molecule is carried out by one of the following techniques: ELISA, fluorimetric immunoassay or radiometric immunoassay.

In embodiments wherein detection is performed using a separate reporter molecule, said reporter molecule may be added to the indicator molecule prior to the addition of the indicator molecule to the test sample. It is preferable that, under these circumstances, the reporter does not interfere with modification, such as cleavage, of the indicator molecule by the enzyme. Alternatively, the indicator molecule may be added to the test sample in the absence of reporter molecule and the reporter molecule is present or added at the time the test sample is exposed to the selective recognition molecules within the selective capture zone. In a further alternative embodiment, the reporter molecule may be added after the test sample containing the indicator molecule has been exposed to the selective recognition molecules within the selective capture zone and has subsequently been transferred into the detection zone.

Detection of indicator molecule present within the detection zone may be facilitated by binding of the indicator molecule to capture molecules present within this zone via the capture site present within the detection region of the indicator molecule. More specifically, binding of any indicator molecules to capture molecules immobilised at a discrete location within the detection zone may allow the person carrying out the method to focus detection of indicator molecules at the level of this discrete location. Binding of indicator molecules to capture molecules present within the detection zone may occur via a direct interaction between the capture site and capture molecule or may be indirect, for example mediated by an adaptor molecule as described elsewhere herein.

In embodiments wherein an adaptor is used to mediate indirect binding of indicator molecules to either reporter molecules or capture molecules or both, this adaptor may be added to the indicator molecule prior to the addition of indicator molecule to the test sample i.e. it may be pre-complexed with the indicator molecule. Alternatively, the adaptor may be added to the device at the time the indicator molecule is exposed to the selective capture zone or to the detection zone of the device.

As detailed above, in preferred embodiments of the invention, the device is configured as a flow device with the selective capture zone and detection zone defined by discrete locations along a chromatographic medium. The test sample may be exposed to the chromatographic medium at a site upstream from the selective capture zone, for example a sample receiving zone. This site or zone may be defined by the presence of a sample pad to which the test sample is applied. In certain embodiments, this sample pad may perform a blood separator function such that certain components of the test sample, for example one or more types of blood cell, are retained within the material of the sample pad and thereby prevented from entering the chromatographic strip.

After application of the test sample to the sample receiving zone, the sample may flow through the selective capture zone and into the detection zone. The sample application zone may be separated from the selective capture zone, for example by means of a soluble barrier, such that the test sample containing the indicator molecule is contacted with the chromatographic medium, for example a nitrocellulose strip, for a period of time before the sample flows through into the selective capture zone. The chromatographic medium may also have attached thereto an adsorbent pad located downstream of the selective capture zone and detection zone. This may act as a reservoir to facilitate the flow of test sample through the zones of the chromatographic medium.

Reporter molecules may be added to the chromatographic medium after the test sample has been allowed to pass through or along the medium. In preferred embodiments, reporter molecules may be pre-associated with the chromatographic medium in a dried form at the time the test sample is applied to the medium. Once the test sample has been left for a period of time to flow through the selective capture zone and detection zone of the device, the reporter molecules may be reconstituted, for example by the addition of a suitable buffer, and thereafter allowed to flow through the chromatographic medium, such that any bound indicator molecules are labelled by subsequent binding of reporter molecules.

The device of the invention may additionally comprise a control capture zone, as described above, comprising control capture molecules. In certain embodiments, the control capture molecules may bind any reporter molecules that are not bound to indicator molecules.

Wherein such a device is used, the methods of the present invention may involve additionally detecting the presence of any reporter molecules bound to control capture molecules within the control capture zone.

For embodiments wherein reporter molecules are used to detect the presence of indicator molecule, the device may also comprise control reporter molecules, as defined above. Such control reporter molecules may be added to the device at the same time as the reporter molecules are added to the device. Wherein the device is a flow device comprising a chromatographic medium, both the reporter molecule and the control reporter molecule may be pre-associated with the chromatographic medium in a dried form at the time the test sample is applied to the medium. Reconstitution of the reporter molecule, for example using a suitable buffer, may be accompanied by reconstitution of the control reporter molecule. Under these circumstances, the device of the invention may further comprise a control capture zone comprising control capture molecules capable of binding the control reporter molecule. Wherein such a device is used, the methods of the present invention may involve additionally detecting the presence of any control reporter molecules bound to control capture molecules within the control capture zone. This "control" readout may be important in order to confirm indirectly that reporter molecules are present and/or functional within the device.

The invention will be further understood with reference to the following clauses:

1. An enzyme detection device for use in the detection of enzyme activity in a test sample comprising:
(i) an indicator molecule for adding to the test sample, said indicator molecule comprising
   (a) an enzyme modifiable region, which can be modified by said enzyme causing transformation of the region from an unmodified to a modified state; and
   (b) a detection region, which is not modified by the enzyme and can be bound by a reporter molecule irrespective of the state of modification of the enzyme modifiable region,
(ii) a selective capture zone to receive the test sample, wherein the selective capture zone comprises selective recognition molecules capable of binding to the enzyme modifiable region of the indicator molecule selectively in one or other of the modified or unmodified states; and
(iii) a detection zone to receive the test sample following contact of the test sample with the selective capture zone, wherein the detection zone is spatially separated from the selective capture zone such that exposure of the test sample to the detection zone occurs after prior exposure of the test sample to the selective capture zone and wherein only indicator molecules that do not bind to the selective recognition molecules in the selective capture zone pass into the detection zone and wherein the indicator molecule is detected at the selective capture zone and/or the detection zone.

2. The device of clause 1 wherein the detection region of the indicator molecule comprises a capture site and the detection zone comprises capture molecules capable of specifically binding to the capture site of the indicator molecule if said indicator molecule is present.

3. The device of clause 1 or 2 wherein the enzyme modifiable region of the indicator molecule comprises a peptide, a protein, a carbohydrate, a lipid or a nucleic acid.

4. The device of any of clauses 1-3 wherein the enzyme to be detected is selected from the following categories: oxidoreductases, transferases, hydrolases, lyases, isomerases and ligases, including the subcategories of protease; peptidase; lipase; nuclease; carbohydrase; phosphatase; sulphatase; neuraminidase; esterase; DNAse; RNAse; kinase; glycosyl transferase; oxidase; reductase; and transaminase.

5. The device of any of clauses 1-4 wherein the enzyme to be detected is a matrix metalloprotease or human neutrophil-derived elastase.

6. The device of any of clauses 1-5 wherein the selective recognition molecule is an antibody or antigen binding fragment thereof, avidin, streptavidin or a derivative thereof, a lectin, a nucleic acid molecule, a receptor molecule, or a hormone binding protein.

7. The device of any of clauses 1-6 wherein the selective capture zone comprises a solid phase support and the selective recognition molecule to which the indicator molecule binds selectively in one or other of the modified states is located on or within the solid phase support.

8. The device of any of clauses 1-7 wherein the enzyme modifiable region cannot be modified by the enzyme once the indicator molecule is bound by a selective recognition molecule.

9. The device of any of clauses 2-8 wherein the capture site of the indicator molecule binds directly to the capture molecules present in the detection zone of the device.

10. The device of clause 9 wherein the capture site and capture molecules are two halves of a binding pair.

11. The device of clause 10 wherein the binding pair is selected from the following: —an antigen and an antibody or antigen binding fragment thereof; biotin and avidin, streptavidin, neutravidin or captavidin; an immunoglobulin or appropriate domain thereof and protein A or G; a carbohydrate and a lectin; complementary nucleotide sequences; a ligand and a receptor molecule; a hormone and hormone binding protein; an enzyme cofactor and an enzyme; an enzyme inhibitor and an enzyme; a cellulose binding domain and cellulose fibres; immobilised aminophenyl boronic acid and cis-diol bearing molecules; and xyloglucan and cellulose fibres and analogues, derivatives and fragments thereof.

12. The device of clause 10 wherein the binding pair is biotin and streptavidin.

13. The device of clause 10 wherein the capture site of the indicator molecule comprises an epitope and the capture molecule comprises an antibody which specifically binds to said epitope.

14. The device of any of clauses 1-13 wherein the detection region of the indicator molecule comprises a reporter moiety.

15. The device of clause 14 wherein the reporter moiety is selected from the following: —a gold particle; a chromogen; a luminescent compound; a fluorescent molecule; a radioactive compound; a visible compound; a liposome or other vesicle containing signal producing substances; an electroactive species; or a combination of enzyme and its substrate.

16. The device of any of clauses 1-13 additionally comprising a reporter molecule bound or capable of binding to the detection region of the indicator molecule.

17. The device of clause 16 wherein the detection region of the indicator molecule comprises a detection site, distinct and spatially separated from the capture site, and the reporter molecule(s) bind(s) to the detection region via the detection site.

18. The device of clause 17 wherein the detection site comprises an epitope, distinct from any epitope present within the capture site, and the reporter molecule comprises an antibody which specifically binds to said epitope.

19. The device of clause 18 wherein the reporter molecule binds to the detection region via the capture site, wherein binding of the reporter molecule to the capture site does not impair the ability of the capture site to bind capture molecules.

20. The device of any of clauses 16-19 wherein the reporter molecule comprises a reporter moiety selected from the following: —a gold particle; a chromogen; a luminescent compound; a fluorescent molecule; a radioactive compound; a visible compound; a liposome or other vesicle containing signal producing substances; an electroactive species; or a combination of enzyme and its substrate.

21. The device of any of clauses 16-20 wherein binding of the reporter molecule to the detection region is indirect and mediated by an adaptor capable of simultaneously binding the detection region and the reporter molecule.

22. The device of clause 21 wherein the adaptor is pre-complexed with the detection region prior to the addition of the test sample to the indicator molecule.

23. The device of clause 21 or 22 wherein the adaptor is streptavidin and the detection region comprises biotin.

24. The device of clause 21 or 22 wherein the adaptor is an adaptor binding pair, said binding pair comprising:
(i) a first member capable of binding to the detection region of the indicator molecule; and
(ii) a second member capable of binding to the first member of the pair and to the reporter molecule.

25. The device of clause 24 wherein the detection region of the indicator molecule comprises biotin, the first member of the adaptor binding pair is avidin or streptavidin, the second member of the adaptor binding pair is biotin, and the reporter molecule comprises a moiety capable of binding biotin.

26. The device of any of clauses 21-25 wherein multiple reporter molecules may bind to each indicator molecule.

27. The device of any of clauses 21-26 wherein the adaptor binds to the capture site within the detection region of the indicator molecule such that the capture site binds indirectly to the capture molecule present in the detection zone of the device via the adaptor.

28. The device of clause 27 wherein the adaptor is streptavidin and the capture molecule is biotin.

29. The device of any of clauses 1-28 wherein the detection zone comprises a solid phase support and the capture molecule is located on or within said solid phase support.

30. The device of any of clauses 1-29 wherein the device is a flow device, and the selective capture zone and detection zone are present at sequential locations along a chromatographic medium.

31. The enzyme detection device of any of clauses 16-30 wherein the detection zone additionally comprises an immobilised recognition molecule to which the reporter molecule binds in the absence of indicator molecule.

32. An indicator molecule for use in the detection of enzyme activity in a test sample comprising:
(i) an enzyme modifiable region, which can be modified by said enzyme causing transformation of the region from an unmodified to a modified state, the unmodified and modified states being structurally distinguishable in terms of binding by a selective recognition molecule;
(ii) a separate capture site which can be bound by a capture molecule irrespective of the state of modification of the enzyme modifiable region; and
(iii) a separate detection site which can be bound by a reporter molecule irrespective of the state of modification of the enzyme modifiable region and irrespective of prior or simultaneous binding of the capture molecule to the capture site.

33. An indicator molecule according to clause 32 for use in an enzyme detection device as defined by any one of clauses 1-30.

34. A method for detecting the presence of enzyme activity in a test sample, the method comprising the steps of:
(i) providing an enzyme detection device comprising an indicator molecule for adding to the test sample, said indicator molecule comprising
   (a) an enzyme modifiable region, which can be modified by said enzyme causing transformation of the region from an unmodified to a modified state; and
   (b) a detection region, which is not modified by the enzyme and can be bound by a reporter molecule irrespective of the state of modification of the enzyme modifiable region;
a selective capture zone to receive the test sample, wherein the selective capture zone comprises selective recognition molecules capable of binding to the enzyme modifiable region of the indicator molecule selectively in one or other of the modified or unmodified states; and
a detection zone to receive the test sample following contact of the test sample with the first capture zone, wherein the detection zone is spatially separated from the first capture zone,
(ii) providing a test sample suspected of containing the enzyme activity;
(iii) adding the indicator molecules of the device to the test sample under conditions in which the enzyme activity, if present, can modify the enzyme modifiable region;
(iv) bringing the test sample into contact with the selective capture zone of the device such that indicator molecules in one or other of the modified or unmodified states are bound to the selective capture molecules thereby allowing separation of either the modified or unmodified form of the indicator molecule from any indicator molecule in the opposite state, if present;
(v) bringing the test sample into contact with the detection zone wherein only indicator molecules that do not bind to the selective capture molecules in the selective capture zone pass into the detection zone; and
(vi) detecting any indicator molecule present within the detection zone and/or selective capture zone.

35. The method of clause 34 wherein the enzyme detection device is as defined in any of clauses 1-31.

36. The method of clause 34 or 35 wherein detection of any indicator molecule in the detection zone is by immunoassay.

37. The method of clause 36 wherein detection of any indicator molecule is by ELISA, fluorimetric immunoassay or radiometric immunoassay.

38. The method of any of clauses 34-37 wherein the detection region of the indicator molecule comprises a capture site and the detection zone comprises capture molecules capable of binding to the capture site of the indicator molecule if said indicator molecule is present.

39. The method of any of clauses 34-38 wherein the selective recognition molecules bind to the indicator molecule in unmodified state and the presence of indicator molecule in the detection zone indicates that enzyme is present in the test sample.

40. Use of an enzyme detection device as defined in any of clauses 1-31 for the detection of enzyme activity in a test sample.

41. An enzyme detection device substantially as herein described with reference to the accompanying drawings.

42. A method for detecting the presence of enzyme activity in a test sample substantially as herein described with reference to the accompanying drawings.

43. Use of an enzyme detection device substantially as herein described with reference to the accompanying drawings.

BRIEF DESCRIPTION OF THE DRAWINGS

The invention will now be described by way of non-limiting example with respect to the accompanying drawings in which.

DESCRIPTION OF PREFERRED EMBODIMENTS

Figure 1:
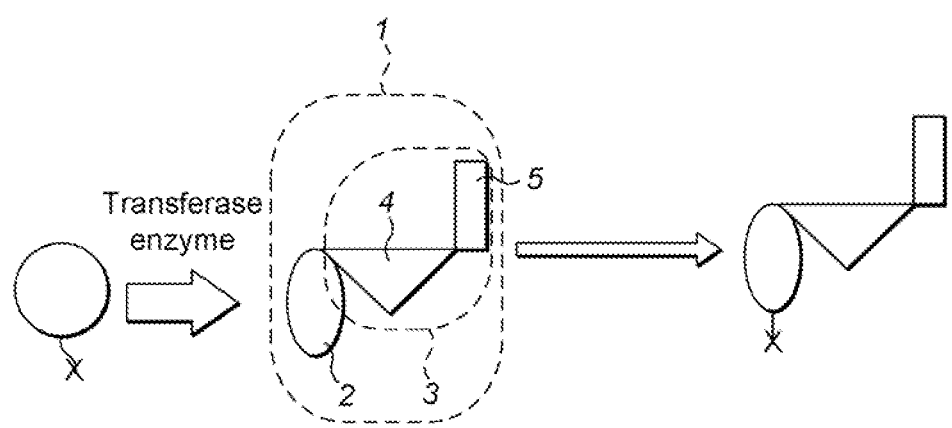
FIG. 1 is a schematic view of an indicator molecule in accordance with one embodiment of the present invention.

FIG. 1 shows an indicator molecule according to a preferred embodiment of the present invention. The indicator molecule (1) as shown comprises an enzyme modifiable region (2) and a detection region (3) comprising a capture site (4) and a separate detection site (5). Modification of the enzyme modifiable region (2) causes transformation of this region from an unmodified to a modified state, wherein these different states are structurally distinguishable by a selective recognition molecule of the present device (discussed herein in detail). In FIG. 1, the enzyme modifiable region (2) is shown undergoing modification by the addition of the chemical group "X" to this region via the action of an enzyme within the transferase family.

Figure 2:
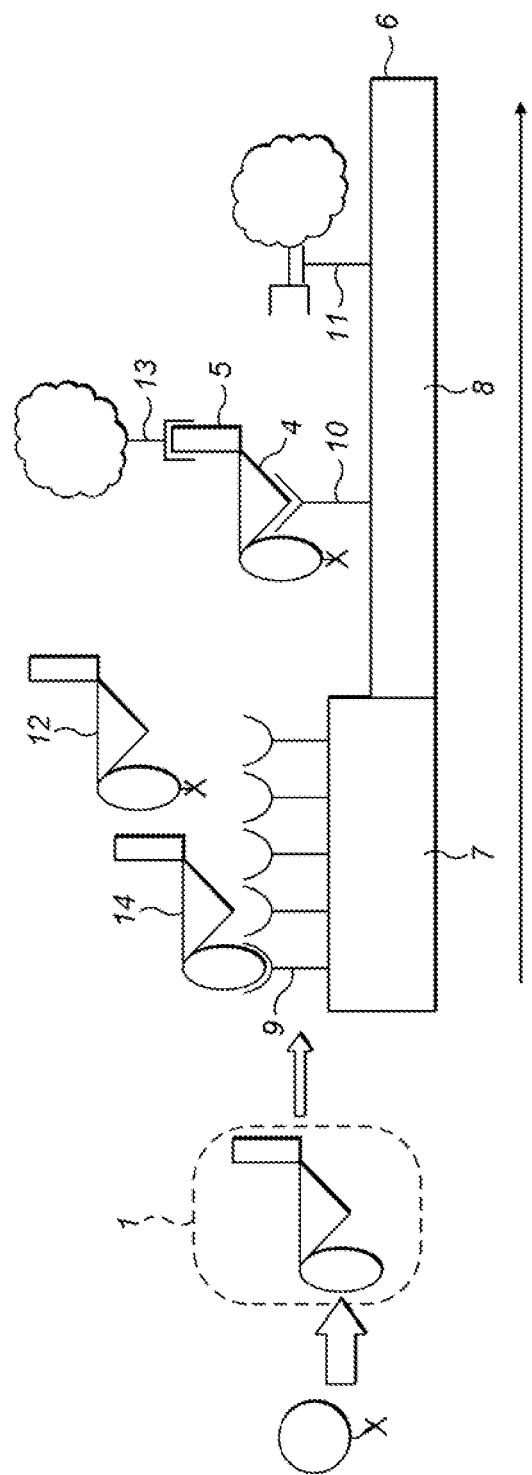
FIG. 2 is a schematic view of an enzyme detection device in accordance with one embodiment of the present invention incorporating the indicator molecule of FIG. 1.

FIG. 2 shows an enzyme detection device according to a preferred embodiment of the present invention. The device comprises an indicator molecule (1) as defined in FIG. 1, and a chromatographic test strip (6) comprising an upstream selective capture zone (7) and a downstream detection zone (8).

In the embodiment of the device shown, the selective capture zone (7) is defined by the presence of selective recognition molecules (9) immobilized by binding to the solid support of the test strip (6). The detection zone (8) is defined by the presence of a capture molecule (10) immobilized at a first site and a further recognition molecule (11) immobilised at a second discrete site. Moreover the detection zone (8) is spatially separated from the selective capture zone (7) by virtue of the immobilization of the respective molecules defining each zone at discrete locations along the long axis of the chromatographic test strip (6).

In use, the indicator molecule (1) may be added to the test sample prior to bringing the test sample into contact with the selective capture zone (7) of the device. The indicator molecule (1), once present in the selective capture zone (7), is only bound by the selective recognition molecules (9) present therein, in one or other of the unmodified or modified states. In the (preferred) embodiment shown in FIG. 2, the selective recognition molecules (9) present in the selective capture zone (7) are only able to bind unmodified indicator molecule (14). Any modified indicator molecule (12), if present, thus remains in "free" or "unbound" form within the selective capture zone (7).

In preferred embodiments of the device, the selective recognition molecules (9) bind to the indicator molecule (1) with high affinity, and in particular, an affinity that is greater than the affinity of the enzyme to be detected for the indicator molecule (1). Moreover, it is preferable that any indicator molecule (1) bound to the selective recognition molecules (9) cannot undergo any subsequent modification by enzymes (to be detected) present within the test sample. Under circumstances in which no further enzymatic modification of the indicator molecule (1) can occur once the test sample is applied to the selective capture zone (7), the signal measured at either zone of the device should not be subject to change over time as a result of continued indicator molecule modification. Thus, the device of the invention may be used as a reliable and accurate end-point assay.

In the preferred embodiment shown in FIG. 2, the device is configured as a lateral flow device. In this embodiment, the test sample is typically applied to the chromatographic test strip (6) at a location upstream from the selective capture zone (7) and is thereafter drawn, by capillary action, along the test strip (6) in the direction indicated by the arrow. Thus, any indicator molecule not captured at the selective capture zone (7) will proceed into the detection zone (8).

In the detection zone (8) of the device, any modified indicator molecule present (12) may be localised by virtue of the binding interaction between the capture site (4) of the indicator molecule and capture molecules (10) present within the detection zone (8). In FIG. 2, a capture molecule (10) is shown immobilised at a discrete location within the region of the chromatographic test strip defined as the detection zone (8). In a preferred embodiment of the invention, the capture site of the indicator molecule comprises an epitope and the capture molecule within the detection zone comprises an antibody, which specifically binds to the epitope present at the capture site.

The presence of indicator molecule (1) may be measured at either zone of the device via the detection region. Detection may be carried out by measuring the signal generated either by a reporter moiety already present within the detection region, or by measuring the signal generated by a reporter molecule bound specifically to the detection region.

In FIG. 2, the detection region of the indicator molecule comprises a distinct detection site (5), and a reporter molecule (13) is shown bound to this site within the detection zone (8) of the device. In preferred embodiments of the invention, the detection site (5) of the indicator molecule comprises an epitope distinct from any epitope found at the capture site, and the reporter molecule comprises an antibody, which specifically binds to the epitope present at the detection site.

The reporter molecule itself may comprise any moiety capable of generating or producing a signal for detection by any suitable means known to those of skill in the art. In preferred embodiments of the invention, the reporter molecule comprises a gold particle conjugated to a molecule capable of specifically binding the detection region of the indicator molecule, for example an antibody as described above.

FIG. 2 also shows a further recognition molecule (11) immobilised on the chromatographic strip at a position within the detection zone (8) downstream from the capture molecule (10). As depicted, this further recognition molecule (11) is able to bind any reporter molecule (13) not bound to indicator molecule. In the absence of signal from any reporter molecules (13) at either the selective capture zone (7) or the detection zone (8 and 10), the detection of reporter molecule signal at this downstream location within the detection zone (8) may be used to confirm that the reporter molecule of the device is capable of generating a positive signal.

Figure 3:
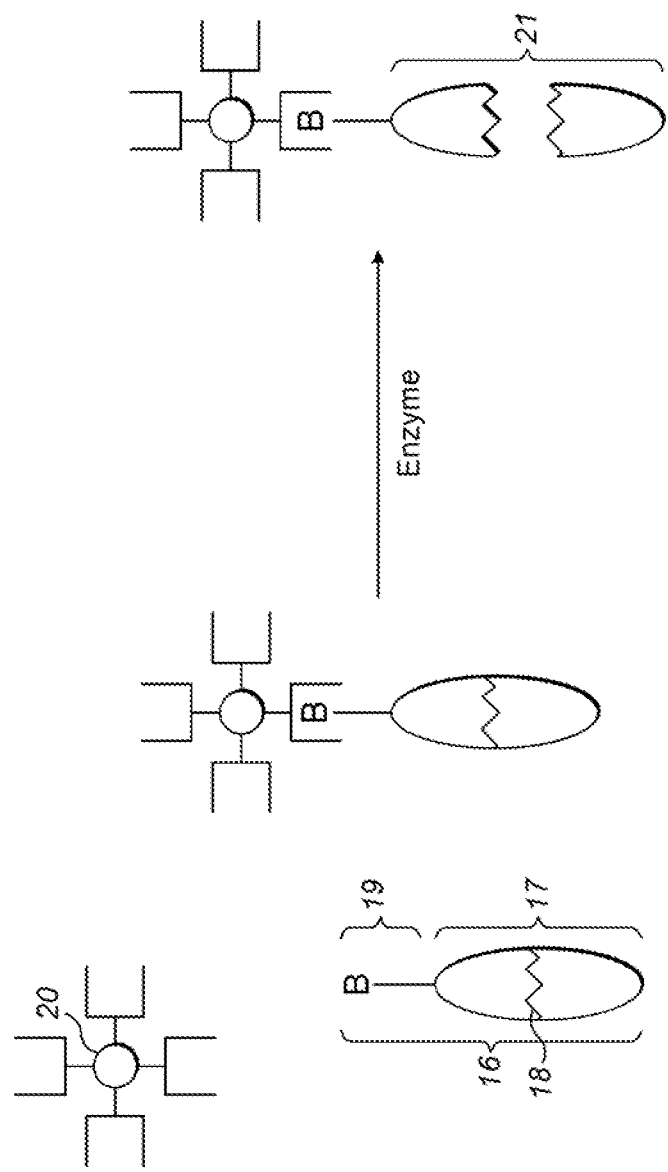
FIG. 3 is a schematic view of an indicator molecule in accordance with a further embodiment of the present invention.

FIG. 3 shows an indicator molecule according to a second preferred embodiment of the present invention. The indicator molecule (16) as shown comprises an enzyme modifiable region (17) containing a single cleavage site (18). In addition, the indicator molecule has a detection region (19). In the embodiment shown, the detection region (19) consists of a biotin moiety (B) and is therefore capable of binding to a multivalent streptavidin adaptor molecule (20). The indicator molecule may be pre-complexed with the adaptor molecule prior to exposure to the test sample suspected to contain the enzyme (as shown). Alternatively, the adaptor molecule (20) may be added to the indicator molecule after enzyme cleavage has occurred.

Once the indicator molecule (16) of the invention is added to a test sample, any enzyme specifically recognising the cleavage site (18) present, may cleave the indicator molecule (16) resulting in transformation of this region from an unmodified (17) to a modified (21) state, wherein these different states are structurally distinguishable by a selective recognition molecule of the present device.

Figure 4:
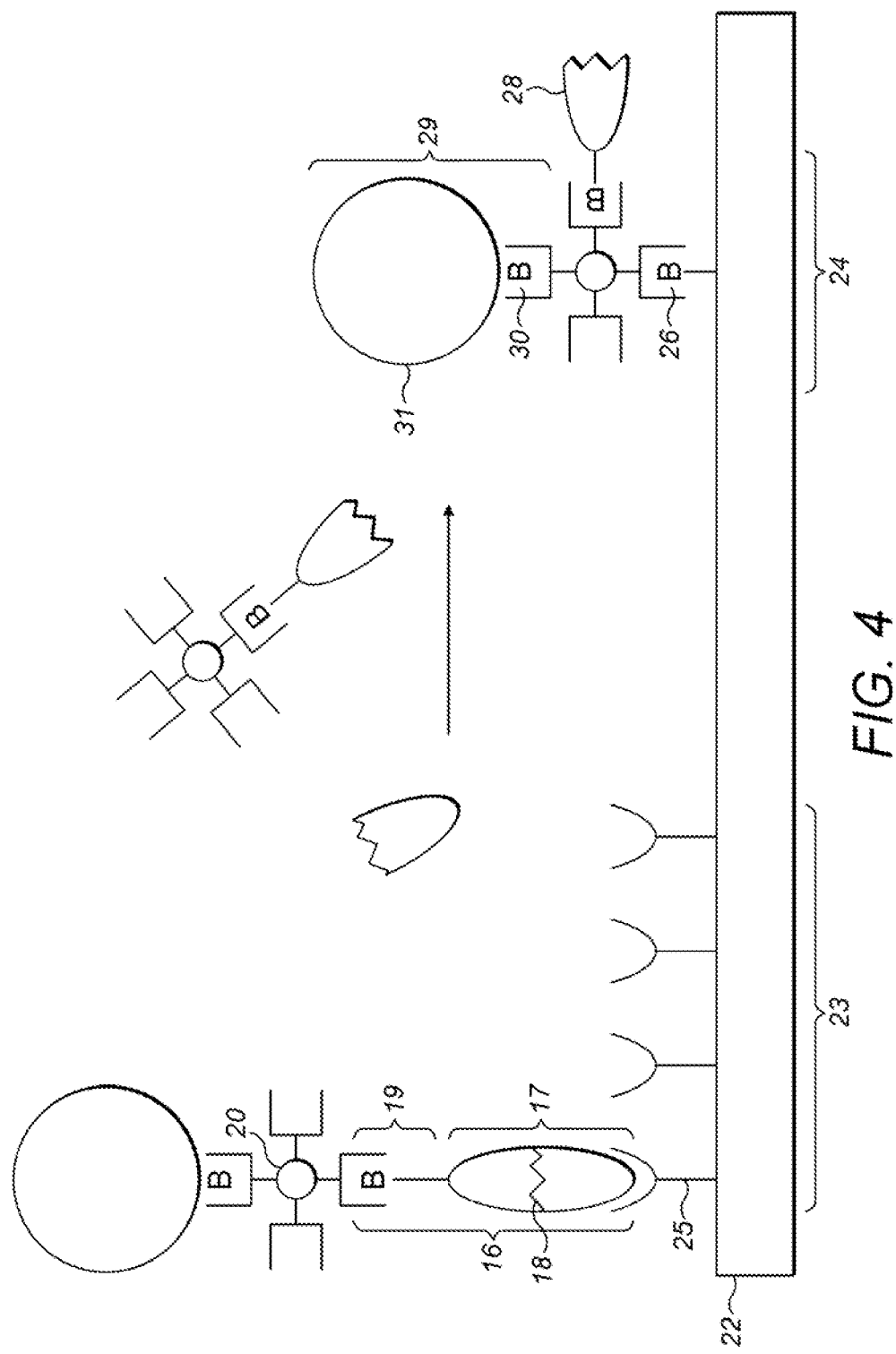
FIG. 4 is a schematic view of an enzyme detection device in accordance with a further embodiment of the present invention incorporating the indicator molecule of FIG. 3.

FIG. 4 shows an enzyme detection device according to a second preferred embodiment of the present invention. The device comprises an indicator molecule (16) as defined in FIG. 3, and a chromatographic test strip (22) comprising an upstream selective capture zone (23) and a downstream detection zone (24).

In the embodiment of the device shown, the selective capture zone (23) is defined by the presence of selective recognition molecules (25) immobilized by binding to the solid support of the test strip (22). The detection zone (24) is defined by the presence of capture molecules (26) and is spatially separated from the selective capture zone (23) by virtue of immobilization of the capture molecules (26) at a discrete downstream location along the long axis of the chromatographic test strip (22).

In use, the indicator molecule (16) is added to the test sample prior to bringing the test sample into contact with the selective capture zone (23) of the device. As shown in FIG. 4, the indicator molecule, once present in the selective capture zone (23) of the device, is able to bind the selective recognition molecules (25) in the unmodified, but not the modified state. In FIG. 4, it is cleavage of the cleavage site (18) of the indicator molecule by any enzyme present in the test sample that prevents recognition of the enzyme modifiable region (17) by the selective recognition molecules (25) in the selective capture zone.

In the preferred embodiment shown, the device is configured as a lateral flow device comprising a chromatographic test strip (22). In this embodiment, the test sample is typically applied to the test strip at a location upstream from the selective capture zone and is thereafter drawn, by capillary action, along the test strip in the direction indicated by the arrow. Thus, any modified forms of the indicator molecule (28) not captured at the selective capture zone (23) will proceed into the detection zone (24).

In the detection zone (24) of the device, cleaved indicator molecule fragments comprising the detection region (28) are localised by virtue of the binding interaction between the capture site (B) present within the detection region (28) and the capture molecules (26) present within the detection zone (24).

In the embodiment of the device shown in FIG. 4, the detection region of the indicator molecule comprises a biotin moiety (B) and is bound by a multivalent streptavidin adaptor molecule (20). This streptavidin adaptor (20) acts as a bridge between the detection region (19) of the indicator molecule and the capture molecule (26), which also comprises a biotin moiety.

In the methods of the present invention, detection of bound unmodified indicator molecule or a cleaved "modified" fragment thereof may be performed at the selective capture zone, the detection zone or both. Detection may be carried out by measuring the signal generated either by a reporter moiety already present within the detection region, or by measuring the signal generated by a reporter molecule bound specifically to the detection region.

In FIG. 4, a reporter molecule (29) is shown bound via a streptavidin adaptor molecule (20) to the detection region of the indicator molecule. The reporter molecule itself comprises a biotin moiety (30), which mediates binding to the streptavidin adaptor, and a gold particle (31) conjugated to said biotin moiety. Alternative means of coupling a reporter molecule to the detection region of the indicator molecule are described in detail above.

In the embodiment shown, the streptavidin adaptor molecule (20) bound to the detection region of the indicator molecule (19) serves a dual purpose at the detection zone in that it mediates binding of the indicator molecule (16) to both the capture molecule (26) and the reporter molecule (29) via their respective biotin moieties.

The invention will be further understood with reference to the following experimental examples.

EXAMPLES

Example 1 A Reverse ELTABA Platform Utilizing a Polystreptavidin: Peptide Complex Indicator Molecule A kit comprises the following components:—
1) A device for sample collection (e.g. for urine)
2) A chase buffer for re-hydrating the gold conjugate consisting of tris buffer saline (TBS) at pH 8.0 and 1% TWEEN™ 20 (Polyoxyethylene (20) sorbitan monolaurate).

3) A lateral flow test-strip, which is mounted in a plastic case. The test strip has a hidden capture zone which comprises a sheep antibody in the form of four pre-absorbent lines (PA lines), a second capture zone which comprises biotin conjugated to a carrier protein as a first test line across the flow-path of the test strip and a third capture zone which comprises anti-chicken antibodies adsorbed as a control line across the flow-path of the test strip, downstream of the test line. There is an observation window in the plastic case through which to view the test and control line. There is also an integrated sample receiving pad, upstream of the first test line. In addition, the test strip has gold particles bearing biotin dried into the test strip upstream of the sample-receiving pad which can be reconstituted by the addition of a buffer in a second well that receives the chase buffer upstream of the gold conjugate pad.

4) A tube, in which the sample collection device may be placed, together with the indicating molecule.

5) An indicator molecule attached to an adapter molecule (which may be incorporated in the sample collection device). The indicator molecule contains the modifiable region, which carries a terminal biotin group, connected via a polyethylene glycol spacer/linker which allows it to form a complex with the adapter molecule, polystreptavidin. The modifiable region is recognised by the sheep antibodies which are immobilised in the hidden capture zone.

The Test Strip

A test strip for the detection of protease activity in a fluid sample was constructed in accordance with the present invention, as described below. The assay is based on the modification of the indicator molecule in the presence of a serine proteinase Human Neutrophil Elastase (HNE) that allows it to form a complex with the test line. Various samples were tested with the strip including wound fluid samples for the detection of protease activity.

A. Preparation of Gold-Impregnated Conjugate Pads

Whatman Glass fiber pad (Whatman, Rapid 24Q, 12 mm×300 mm) was sprayed with biotin: 40 nm gold conjugate (Innova Bioscience) at OD4, and Chicken IgY Gold conjugate (Mologic) at OD2, diluted in gold drying buffer (50 mM Tris, 150 mM sodium chloride, 20 mM sodium Azide, 1% BSA, 10% Trehalose dihydrate, 1% TWEEN™ 20 (Polyoxyethylene (20) sorbitan monolaurate) at pH 8.0) at 0.9 µl/mm with the Isoflow dispenser (7 mm spray height). Processed conjugate band was dried in a tunnel dryer at 60° C. at a speed of 5 mm/sec. The dried gold conjugate-impregnated conjugate pads were stored dried in a sealed foil pouch with desiccant at room temperature.

B. Preparation of Antibody-Impregnated Nitrocellulose Membrane

All reagents were striped on Millipore HF090 membrane (Millipore, HF09004S40, 40×300 mm) at a dispense rate of 0.05 µl/mm. PA lines comprised of 1 mg/ml CF1060 (Mologic) at 10, 12, 14 and 16 mm from base of membrane, Test line BSA biotin (Mologic) at a concentration of 0.4 mg/ml at 23 mm from base of membrane and control line Goat anti Chicken IgY (Lampire, 7455207) at a concentration of 0.5 mg/ml at 28 mm from base of membrane. Processed membrane was dried in a tunnel dryer at 60° C. at a speed of 10 mm/sec. The dried antibody-impregnated Nitrocellulose Membrane was stored in a sealed foil pouch with desiccant at room temperature.

C. Chase Buffer

Aq. Solution of 50 mM Tris, 150 mM sodium chloride, 20 mM sodium azide, 1% vol/vol TWEEN™ 20 (Polyoxyethylene (20) sorbitan monolaurate), at pH 8.0.

D. Card Assembly

Figure 5:
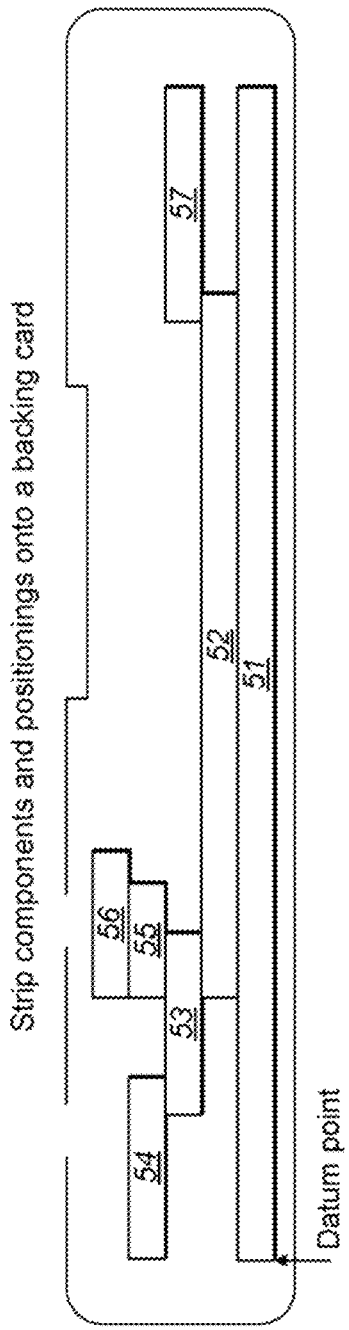
FIG. 5 shows the arrangement of a chromatographic strip for use in conjunction with the enzyme detection device of the present invention.

A test card was assembled according to the following procedure and in accordance with FIG. 5 which specifies the exact longitudinal dimensions and position of each of the card components. Following preparation, the card was trimmed to obtain a plurality of strips for protease assay.

1. A 75×300 mm piece of clear plastic film with a release liner protected adhesive, serving as the back laminate (51) (G&L Precision Die Cutting, 28840) was placed on top of a worktable. The release liner was peeled to expose the adhesive side of the tape.
2. The reaction membrane (52), prepared as in section B, was attached on top of the adhesive side of the back cover (51), 16 mm from the lower end.
3. The impregnated conjugate pad (53), prepared as in section A was attached on top of the back cover (51) with 1 mm overlap on top of the reaction membrane (52).
4. The buffer pad (54, Whatman, CF5, 11×300 mm) was placed on top of the back cover (51) with 6 mm overlap on top of the conjugate pad (53).
5. The double sided tape (55, G&L Precision Die Cutting, GL-187) was attached over the conjugate pad (53) 15 mm from the lower end.
6. The sample receiving pad/blood separator membrane (56, Spectral SG membrane, Primecare) was placed over the tape (55) with cover removed, 15 mm from the lower end.
7. The absorbent pad (57, Gel blotting paper, Ahlstrom, grade 222, 23×300 mm) was placed on top of the upper side of the back cover (51) with a 3 mm overlap on top of the reaction membrane (52).

The card was trimmed to 4 mm width strips using an automated die cutter (Kinematic, 2360) and assembled into 2 well plastic housings (BBI Dundee, vision). The devices were closed using a pneumatic device clamp specifically manufactured for these devices at Mologic.

In the example described below, buffer standards were produced containing different concentrations of HNE (Lee biotech, 342-40) ranging from 2000 ng/ml down to 62.5 ng/ml.

STEP 1: A sample of fluid (the test sample) was placed in a collection device with a defined amount of peptide (6 ng/test) pre-complexed with the adaptor protein (100 ng/test). The ratio of peptide to adaptor protein was pre-determined to ensure optimal binding. The collection device was rotated vigorously in order for the sample to mix sufficiently with the substrate solution. This reaction mixture was incubated at ambient temperature for a defined period of time (e.g. 10 minutes).

STEP 2: At the end of the incubation period, a defined volume of liquid was dropped onto the sample receiving pad (56). As the liquid migrated onto the test strip any intact indicator molecule was recognised and captured by the pre-absorbent lines in the hidden capture zone. Where the substrate region had been damaged by HNE in the sample, the indicator molecule migrated towards the biotin test line where it was immobilised via the polystreptavidin adaptor protein.

STEP 3: Once the sample had traveled through the test strip (52) aided by the absorbent pad (57) that acted as a reservoir, two drops of the chase buffer provided in the kit was added to a buffer pad (54) that made contact with and re-hydrated the dried biotin attached to the gold particles. As the conjugated gold particles entered the hidden capture zone any intact indicator molecule bound to the pre-absorbent lines was labelled via the polystreptavidin adaptor protein. Those that had not bound to the intact indicator molecule in the hidden capture zone migrated down the strip and labelled any indicator molecule captured by the test line. A separate control system was used that comprised chicken IgY attached to gold particles which bound to a Goat anti Chicken IgY control line. The presence of a line indicated that the test was complete.

The lines that were formed were assessed by their relative intensities. The presence of a test line and the presence of a full strength control line indicated that there was protease present in the test sample. A negative test line indicated a zero or low level of protease that was below the detectable limit. Stages in between these extremes indicated different levels of protease in the test sample. The intensity of the developed coloured lines was measured visually and with an NES Lateral flow device reader. A semi-quantitative scoring system with a scale of 0-10, in which 1 was the lowest detectable colour intensity and 10 was the highest observed colour intensity was used for the visual readings.

Figure 6:
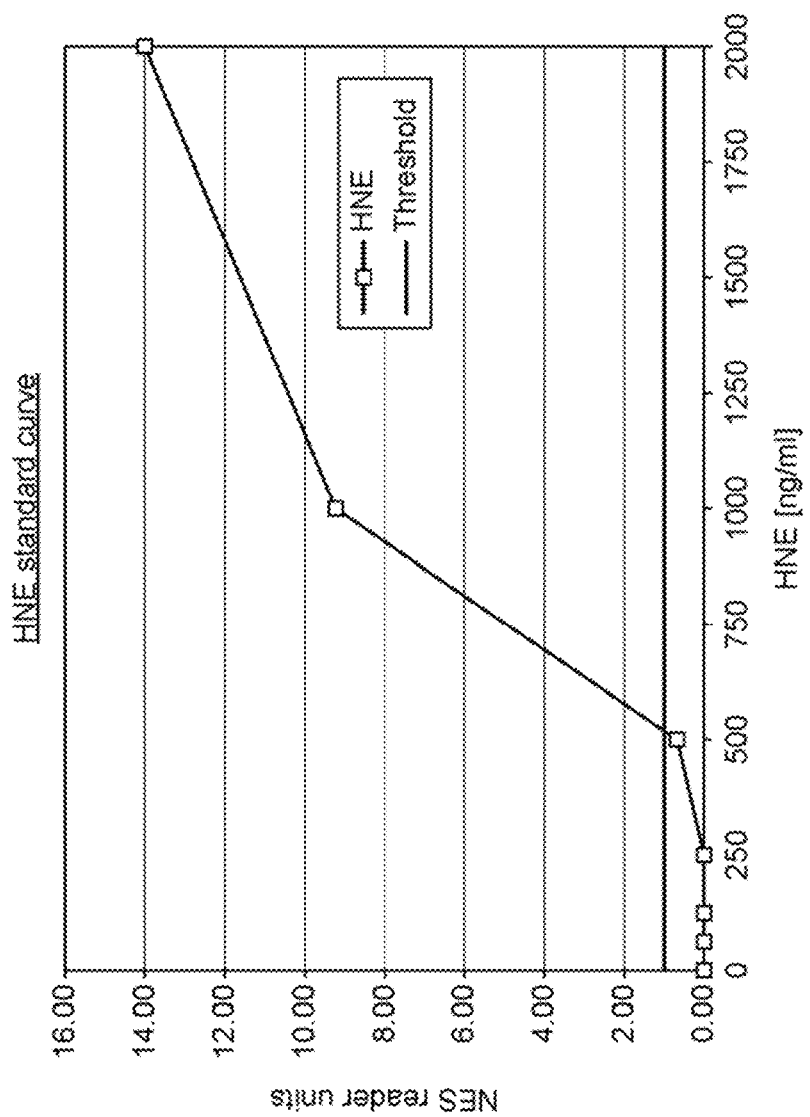
FIG. 6 shows results produced using an enzyme detection device according to the present invention to detect Human neutrophil elastase (HNE) activity.

FIG. 6 demonstrates the sensitivity of the assay when run with spiked HNE buffer samples. The detectable limit for HNE was approximately 500-1000 ng/ml with a sample volume of 20 µl. The reader units are displayed where a value above 1 is deemed a positive.

Example 2 A Reverse ELTABA Platform Utilizing Polystreptavidin: Peptide Complex Indicator Molecules Having One or More Cleavage Sites for the Detection of Matrix Metalloprotease-9 (MMP-9)

A kit comprises the following components:—
1) A device for sample collection (e.g. for urine)
2) A chase buffer for re-hydrating the gold conjugate consisting of Tris buffer saline (TBS) at pH 8.0 and 1% TWEEN™ 20 (Polyoxyethylene (20) sorbitan monolaurate).
3) A lateral flow test-strip, which is mounted in a plastic case. The test strip has a hidden capture zone which comprises of a sheep antibody in the form of four pre-absorbent lines (PA lines), a second capture zone which comprises biotin conjugated to a carrier protein as a first test line across the flow-path of the test strip and a third capture zone which comprises anti chicken antibodies adsorbed as a control line across the flow-path of the test strip, downstream of the test line. There is an observation window in the plastic case through which to view the test and control line. There is also an integrated sample receiving pad, upstream of the first test line. In addition, the test strip has gold particles bearing biotin dried into the test strip upstream of the sample-receiving pad which can be reconstituted by the addition of a buffer in a second well that receives the chase buffer upstream of the gold conjugate pad.
4) A tube, in which the sample collection device may be placed, together with the indicator molecule.
5) An indicator molecule, (which may be incorporated in the sample collection device). The indicator molecule consists of peptide containing a sequence of amino acids biased for MMP-9, GPQGIFGQ (SEQ ID NO:1). The indicator molecule carries a terminal biotin group, connected via a polyethylene glycol spacer/linker which allows it to form a complex with the adapter molecule, polystreptavidin. Also incorporated is the $1^{st}$ capture region (ALP) which is recognised by the sheep antibodies which are immobilised in the hidden capture zone. Different indicator molecules were used having different numbers of MMP9 cleavage sites present, in particular, 1, 2, 3, 5 and 7 MMP9 cleavage sites.
6) An adapter molecule e.g. polystreptavidin that contains multiple binding regions that can form a complex with the indicator molecule that contains the cleavage site(s).

The Test Strip

A test strip for the detection of protease activity in a fluid sample was constructed in accordance with the present invention, as described below. The assay is based on the cleavage of the indicator molecule in the presence of MMP-9 to yield a fragment that will bind to the test line. Various samples were tested with the strip including wound fluid samples for the detection of protease activity.

A. Preparation of Gold-Impregnated Conjugate Pads

Whatman Glass fiber pad (Whatman, Rapid 24Q, 12 mm×300 mm) was sprayed with biotin: 40 nm gold conjugate (Innova Bioscience) at OD4, and Chicken IgY Gold conjugate (Mologic) at OD2, diluted in gold drying buffer (50 mM Tris, 150 mM sodium chloride, 20 mM sodium Azide, 1% BSA, 10% Trehalose dihydrate, 1% TWEEN™ 20 (Polyoxyethylene (20) sorbitan monolaurate) at pH 8.0) at 0.9 µl/mm with the Isoflow dispenser (7 mm spray height). Processed conjugate band was dried in a tunnel dryer at 60° C. at a speed of 5 mm/sec. The dried gold conjugate-impregnated conjugate pads were stored in a sealed foil pouch with desiccant at room temperature.

B. Preparation of Antibody-Impregnated Nitrocellulose Membrane

All reagents were striped on Millipore HF090 membrane (Millipore, HF09004S40, 40×300 mm) at a dispense rate of 0.05 µl/mm. PA lines comprised of 1 mg/ml CF1060 (Mologic) at 10, 12, 14 and 16 mm from base of membrane. Test line BSA biotin (Mologic) at a concentration of 0.4 mg/ml at 23 mm from base of membrane and control line Goat anti Chicken IgY (Lampire, 7455207) at a concentration of 0.5 mg/ml at 28 mm from base of membrane. Processed membrane was dried in a tunnel dryer at 60° C. at a speed of 10 mm/sec. The dried antibody-impregnated Nitrocellulose Membrane was stored in a sealed foil pouch with desiccant at room temperature.

C. Chase Buffer

Aq. Solution of 50 mM Tris, 150 mM sodium chloride, 20 mM sodium azide, 1% vol/vol TWEEN™ 20 (Polyoxyethylene (20) sorbitan monolaurate), at pH 8.0.

D. Card Assembly

A test card was assembled according to the following procedure and in accordance with FIG. 5, which specifies the exact longitudinal dimensions and position of each of the card components. Following preparation, the card was trimmed to obtain a plurality of strips for protease assay.

1. A 75×300 mm piece of clear plastic film with a release liner protected adhesive, serving as the back laminate (51) (G&L Precision Die Cutting, 28840) was placed on top of a worktable. The release liner was peeled to expose the adhesive side of the tape.
2. The reaction membrane (52), prepared as in section B, was attached on top of the adhesive side of the back cover (51), 16 mm from the lower end.
3. The impregnated conjugate pad (53), prepared as in section A, was attached on top of the back cover (51) with 1 mm overlap on top of the reaction membrane (52).
4. The buffer pad (54, Whatman, CF5, 11×300 mm) was placed on top of the back cover (51) with 6 mm overlap on top of the conjugate pad (53).
5. The double sided tape (55, G&L Precision Die Cutting, GL-187) was attached over the conjugate pad (53) 15 mm from the lower end.

6. The sample receiving pad/blood separator membrane (56, Spectral SG membrane, Primecare) was placed over the tape (55) with cover removed, 15 mm from the lower end.
7. The absorbent pad (57, Gel blotting paper, Ahlstrom, grade 222, 23×300 mm) was placed on top of the upper side of the back cover (51) with a 3 mm overlap on top of the reaction membrane (52).

The card was trimmed to 4 mm width strips using an automated die cutter (Kinematic, 2360) and assembled into 2 well plastic housings (BBI Dundee, vision). The devices were closed using a pneumatic device clamp specifically manufactured for these devices at Mologic.

In the example described below, buffer standards were produced containing different concentrations of MMP-9 (Mologic) ranging from 2000 ng/ml down to 31.25 ng/ml.

STEP 1: A sample of fluid (the test sample) was placed in a collection device with a defined amount of peptide (6 ng/test). The collection device was rotated vigorously in order for the sample to mix sufficiently with the indicator molecule. This reaction mixture was incubated at ambient temperature for a defined period of time (e.g. 10 minutes) after which the adapter molecule (100 ng/test) was subsequently added which formed complexes with the biotin on the indicator molecule.

STEP 2: At the end of the incubation period, a defined volume of liquid was dropped onto the sample receiving pad (56). The indicator molecule which was added to the sample prior to the incubation period was able to bind to the sheep antibodies (CF1060) in the hidden capture zone via the $1^{st}$ capture region. Any MMP-9 present in the sample cleaved the indicator molecule at the cleavage site(s), allowing the release of the cleaved fragment from the hidden capture zone. The cleaved fragment migrated towards the biotin test line where it was immobilised via the polystreptavidin adapter molecule.

STEP 3: Once the sample had traveled through the test strip (52) aided by the absorbent pad (57) that acted as a reservoir, two drops of the chase buffer provided in the kit was added to a buffer pad (54) that made contact with and re-hydrated the dried biotin attached to the gold particles. As the conjugated gold particles entered the hidden capture zone any intact indicator molecule bound to the pre-absorbent lines was labelled via the polystreptavidin adaptor molecule. Those that had not bound to the intact indicator molecule in the hidden capture zone migrated down the strip and labelled any adaptor molecule captured by the test line. A separate control system was used that comprised chicken IgY attached to gold particles which bound to a Goat anti Chicken IgY control line. The presence of a line indicated that the test was complete.

The lines that were formed were assessed by their relative intensities. The presence of a test line and the presence of a full strength control line indicated that there was protease present in the test sample. A negative test line indicated a zero or low level of protease that was below the detectable limit. Stages in between these extremes indicated different levels of protease in the test sample. The intensity of the developed coloured lines was measured visually and with an NES Lateral flow device reader.

Figure 7A:
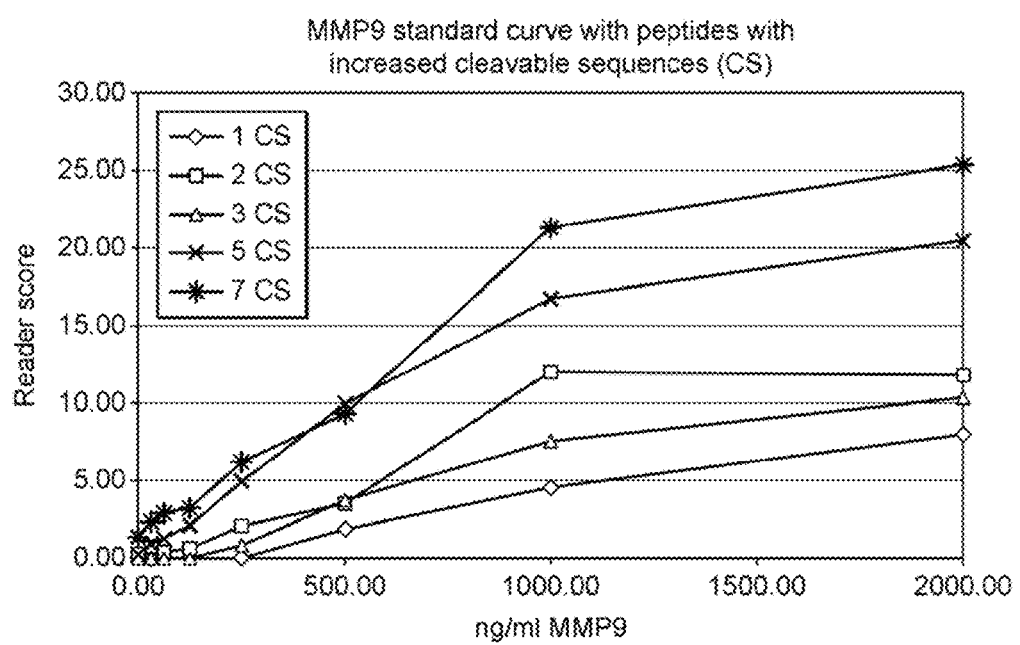
FIG. 7 shows results produced using indicator molecules according to the present invention containing 1, 2, 3, 5 and 7 cleavage sites, used to detect MMP9 activity.
Figures 7B, 7C:
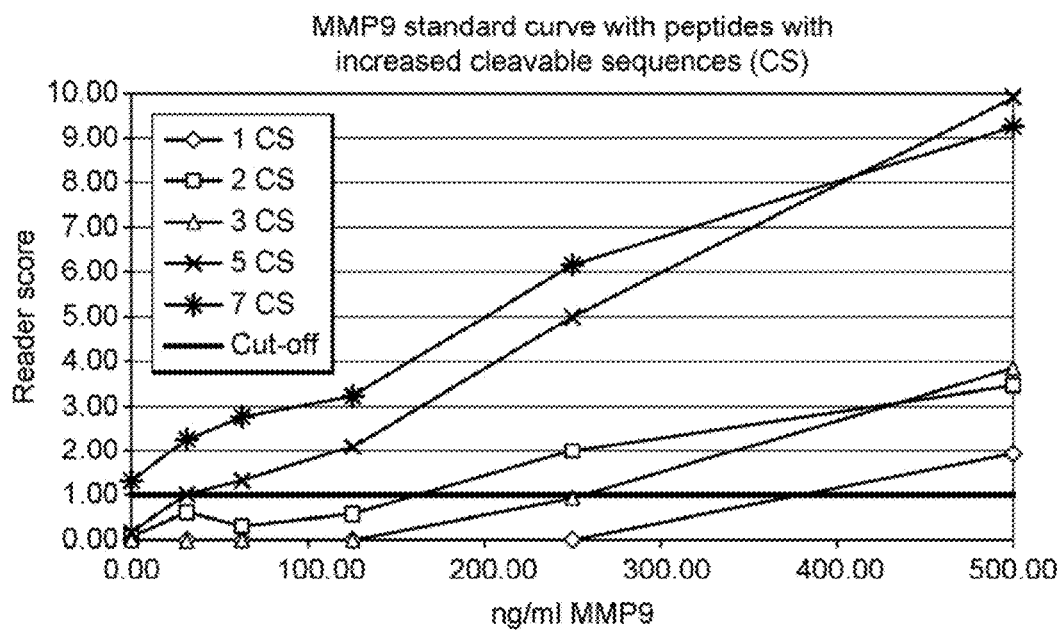

The results are shown in Table 1 and FIG. 7.

TABLE 1

| ng/ml MMP9 | 1 CS | 2CS | 3CS | 5CS | 7CS |
|---|---|---|---|---|---|
| 0 | 0.00 | 0.00 | 0.00 | 0.21 | 1.34 |
| 31.25 | 0.00 | 0.68 | 0.00 | 1.04 | 2.27 |

TABLE 1-continued

| ng/ml MMP9 | 1 CS | 2CS | 3CS | 5CS | 7CS |
|---|---|---|---|---|---|
| 62.5 | 0.00 | 0.32 | 0.00 | 1.36 | 2.81 |
| 125 | 0.00 | 0.57 | 0.00 | 2.14 | 3.25 |
| 250 | 0.00 | 1.99 | 0.92 | 5.01 | 6.19 |
| 500 | 1.93 | 3.48 | 3.84 | 9.93 | 9.31 |
| 1000 | 4.52 | 11.98 | 7.57 | 16.78 | 21.27 |
| 2000 | 8.00 | 11.76 | 10.49 | 20.48 | 25.34 |

FIG. 7 shows the sensitivity of the assay when run with spiked MMP9 buffer samples and indicator molecules having 1, 2, 3, 5 and 7 MMP9 cleavage sites. The sensitivity increases from 250-500 ng/ml MMP9, seen with an indicator molecule having 1 cleavage site, to <31.25 ng/ml for an indicator molecule having 7 cleavage sites.

Example 3 A Reverse ELTABA Platform Utilizing a Synthetic Peptide Indicator Molecule Consisting of One or More Cleavage Sites for the Detection of Matrix Metalloprotease-9 (MMP-9)

A kit comprises the following components:—
1) A device for sample collection (e.g. for urine)
2) A chase buffer for re-hydrating the gold conjugate consisting of Tris buffer saline (TBS) at pH 8.0 and 1% TWEEN™ 20 (Polyoxyethylene (20) sorbitan monolaurate).
3) A lateral flow test-strip, which is mounted in a plastic case. The test strip has a hidden capture zone which comprises of polystreptavidin in the form of four pre-absorbent lines (PA lines), a second capture zone which comprises anti-DNP as a first test line across the flow-path of the test strip and a third capture zone which comprises anti chicken antibodies adsorbed as a control line across the flow-path of the test strip, downstream of the test line. There is an observation window in the plastic case through which to view the test and control line. There is also an integrated sample receiving pad, upstream of the first test line. In addition, the test strip has gold particles bearing anti-FITC dried into the test strip upstream of the sample-receiving pad, which can be reconstituted by the addition of a buffer in a second well that receives the chase buffer upstream of the gold conjugate pad.
4) A test tube, in which the sample collection device may be placed, together with the indicating molecule.
5) An indicator molecule (which may be incorporated in the sample collection device). The indicator molecule consists of a peptide containing a sequence of amino acids biased for MMP-9 i.e. GPQGIFGQ (SEQ ID NO:1), a DNP that acts as a $2^{nd}$ capture site and finally a fluorescent label that is the detection site. The peptide carries a terminal biotin group, connected via a polyethylene glycol spacer/linker that is recognised by the polystreptavidin immobilised in the hidden capture zone. Additional indicator molecules were also used including peptides containing 2, 3 and 4 MMP9 cleavage sites. These experiments were carried out in order to test the sensitivity of the assay using indicator molecules having multiple cleavage sites.

The Test Strip

A test strip for the detection of protease activity in a fluid sample was constructed in accordance with the present invention, as described below. The assay is based on the cleavage of the indicator molecule in the presence of MMP-9 to yield a fragment that will bind to the test line. Various samples were tested with the strip including wound fluid samples for the detection of protease activity.

A. Preparation of Gold-Impregnated Conjugate Pads

Whatman Glass fiber pad (Whatman, Rapid 24Q, 12 mm×300 mm) was sprayed with anti FITC gold conjugate (Mologic) at OD4 and Chicken IgY Gold conjugate (Mologic) at OD2 diluted in gold drying buffer (50 mM Tris, 150 mM sodium chloride, 20 mM sodium Azide, 1% BSA, 10% Trehalose dihydrate, 1% TWEEN™ 20 (Polyoxyethylene (20) sorbitan monolaurate) at pH 8.0) at 0.6 µl/mm with the Isoflow dispenser (7 mm spray height). Processed conjugate band was dried in a tunnel dryer at 60° C. at a speed of 5 mm/sec. The dried gold conjugate-impregnated conjugate pads were stored in a sealed foil pouch with desiccant at room temperature.

B. Preparation of Antibody-Impregnated Nitrocellulose Membrane

All reagents were striped on Millipore HF090 membrane (Millipore, HF09004S40, 40×300 mm) at a dispense rate of 0.05 µl/mm. PA lines comprised of 1 mg/ml Polystreptavidin (BBI, Dundee, 01041049L) at 10, 12, 14 and 16 mm from base of membrane, Test line Goat anti DNP (Bethyl labs, A150117A) at a concentration of 1 mg/ml at 23 mm from base of membrane and control line anti Chicken IgY (Lampire, 7455207) at a concentration of 0.5 mg/ml at 28 mm from base of membrane. Processed membrane was dried in a tunnel dryer at 60° C. at a speed of 10 mm/sec. The dried antibody-impregnated Nitrocellulose Membrane was stored dried in a sealed foil pouch with desiccant at room temperature.

C. Chase Buffer

Aq. Solution of 50 mM Tris, 150 mM sodium chloride, 20 mM sodium azide, 1% vol/vol TWEEN™ 20 (Polyoxyethylene (20) sorbitan monolaurate), at pH 8.0.

D. Card Assembly

A test card was assembled according to the following procedure and in accordance with FIG. 5 which specifies the exact longitudinal dimensions and position of each of the card components. Following preparation, the card was trimmed to obtain a plurality of strips for protease assay.

1. A 75×300 mm piece of clear plastic film with a release liner protected adhesive, serving as the back laminate (51) (G&L Precision Die Cutting, 28840) was placed on top of a worktable. The release liner was peeled to expose the adhesive side of the tape.
2. The reaction membrane (52), prepared as in section B, was attached on top of the adhesive side of the back cover (51), 16 mm from the lower end.
3. The impregnated conjugate pad (53), prepared as in section A was attached on top of the back cover (51) with 1 mm overlap on top of the reaction membrane (52).
4. The buffer pad (54, Whatman, CF5, 11×300 mm) was placed on top of the back cover (51) with 6 mm overlap on top of the conjugate pad (53).
5. The double sided tape (55, G&L Precision Die Cutting, GL-187) was attached over the conjugate pad (53) 15 mm from the lower end.
6. The sample receiving pad/blood separator membrane (56, Spectral SG membrane, Primecare) was placed over the tape (55) with cover removed, 15 mm from the lower end.
7. The absorbent pad (57, Gel blotting paper, Ahlstrom, grade 222, 23×300 mm) was placed on top of the upper side of the back cover (51) with a 3 mm overlap on top of the reaction membrane (52).

The card was trimmed to 4 mm width strips using an automated die cutter (Kinematic, 2360) and assembled into 2 well plastic housings (BBI Dundee, vision). The devices were closed using a pneumatic device clamp specifically manufactured for these devices at Mologic.

Buffer standards were produced containing different concentrations of MMP-9 (Mologic) ranging from 2000 ng/ml down to 7.8 ng/ml.

STEP 1: A sample of fluid (the test sample) was placed in a collection device with a defined amount of indicator molecule (400 pg/test). The collection device was rotated vigorously in order for the sample to mix sufficiently with the indicator molecule. This reaction mixture was incubated at ambient temperature for a defined period of time (e.g. 10 minutes).

STEP 2: At the end of the incubation period, a defined volume of liquid was dropped onto the sample receiving pad (56). The indicator molecule which was added to the sample prior to the incubation period was able to bind to the polystreptavin in the hidden capture zone via the $1^{st}$ capture region. Any MMP-9 present in the sample cleaved the indicator molecule at the cleavage site(s), allowing the release of the cleaved fragment from the hidden capture zone. The cleaved fragment migrated towards the anti-DNP test line where it was immobilised via the DNP capture site.

STEP 3: Once the sample had traveled through the test strip (52) aided by the absorbent pad (57) that acted as a reservoir, two drops of the chase buffer provided in the kit was added to a buffer pad (54) that made contact with and re-hydrated the dried anti-FITC attached to the gold particles. As the conjugated gold particles entered the hidden capture zone any intact indicator molecule bound to the pre-absorbent lines was labelled via the fluorescent label detection site. Those that had not bound to the intact indicator molecule in the hidden capture zone migrated down the strip and labelled any cleaved indicator molecule captured by the test line. A separate control system was used that comprised of chicken IgY attached to gold particles which bound to a Goat anti Chicken IgY control line. The presence of a line indicated that the test was complete.

The lines that were formed were assessed by their relative intensities. The presence of a test line and the presence of a full strength control line indicated that there was protease present in the test sample. A negative test line indicated a zero or low level of protease that was below the detectable limit. Stages in between these extremes indicated different levels of protease in the test sample. The intensity of the developed coloured lines was measured visually and with an NES Lateral flow device reader. The results are shown in Table 2 and FIG. 8.

TABLE 2

| ng/ml MMP9 | 1 CS | 2CS | 3CS | 4CS |
|---|---|---|---|---|
| 0 | 0.51 | 0.94 | 0.94 | 1.12 |
| 31.25 | 1.37 | 1.36 | 1.45 | 2.69 |
| 62.5 | 1.28 | 1.78 | 2.56 | 2.94 |
| 125 | 2.01 | 3.46 | 3.10 | 5.63 |
| 250 | 3.34 | 5.44 | 5.58 | 10.05 |
| 500 | 3.73 | 6.87 | 9.04 | 11.20 |
| 1000 | 4.33 | 5.48 | 11.62 | 16.30 |
| 2000 | 8.70 | 12.80 | 17.92 | 16.20 |

Figure 8A:
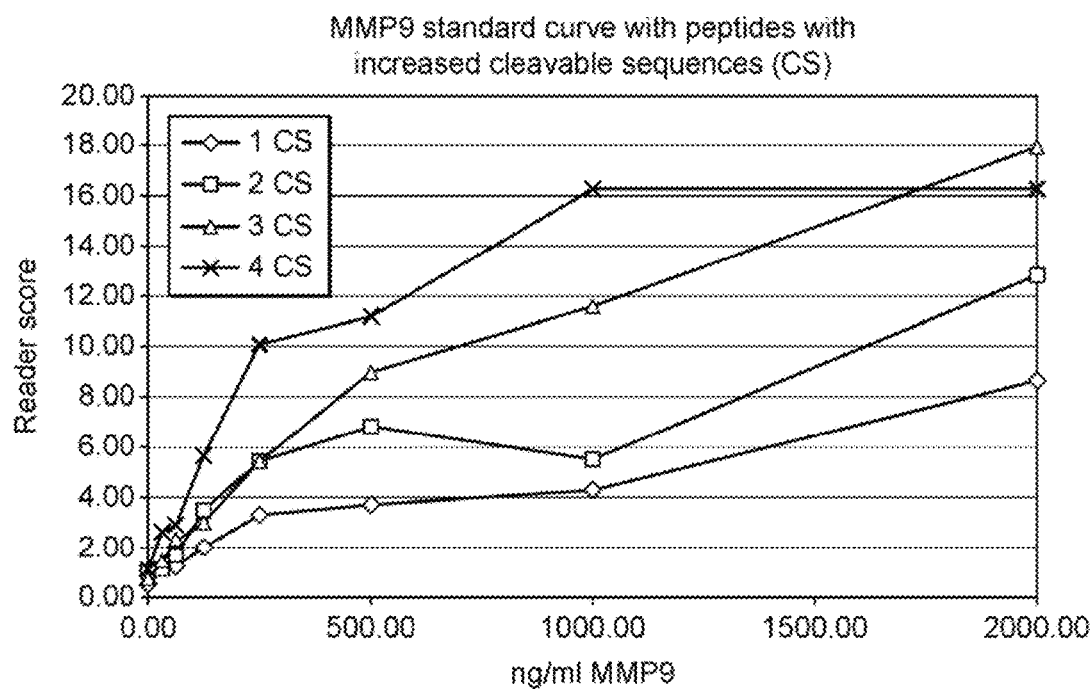
FIG. 8 shows results produced using indicator molecules according to the present invention containing 1, 2, 3 and 4 cleavage sites, used to detect MMP9 activity.
Figure 8B:
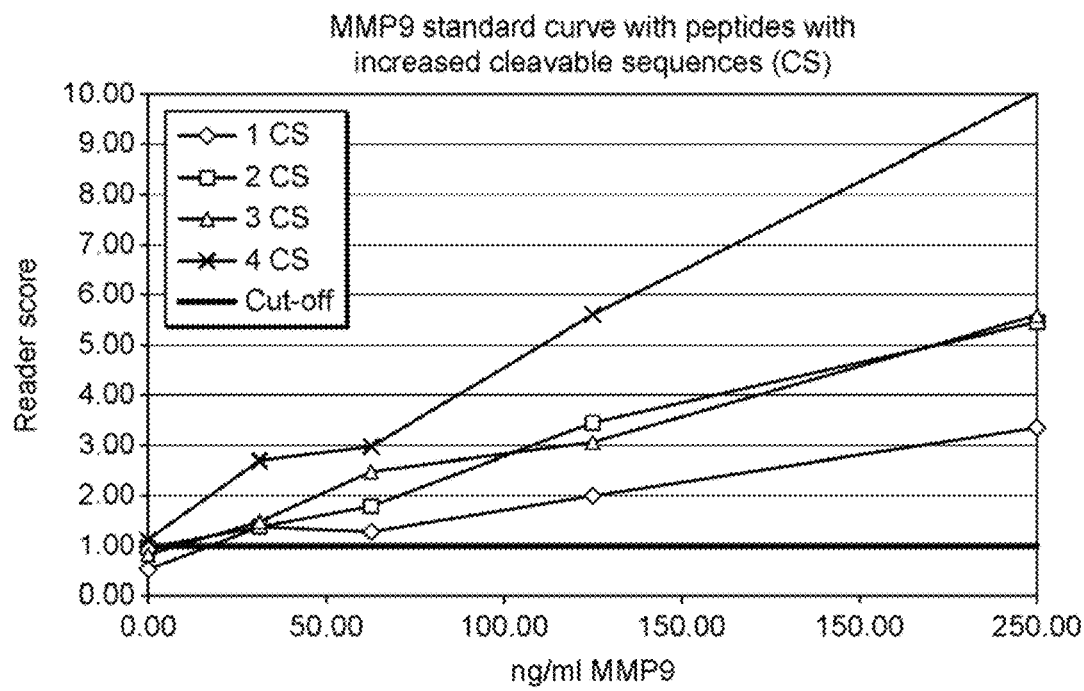

FIG. 8 shows the sensitivity of the assay when run with spiked MMP9 buffer samples and indicator molecules having 1, 2, 3, and 4 MMP9 cleavage sites. The cut-off with all indicator molecules was below <31.25 ng/ml, with the assay including the peptide having 4 cleavage sites appearing more sensitive. The signal intensity increased with increasing numbers of cleavage sites, particularly at the lower levels of MMP9 giving a more defined cut-off.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Moreover, all aspects and embodiments of the invention described herein are considered to be broadly applicable and combinable with any and all other consistent embodiments, including those taken from other aspects of the invention (including in isolation) as appropriate. Various publications are cited herein, the disclosures of which are incorporated by reference in their entireties.

The invention claimed is:

1. An enzyme detection device for use in the detection of enzyme activity in a test sample comprising:
   (i) an indicator molecule for adding to the test sample, said indicator molecule comprising
      (a) an enzyme modifiable region, which can be modified by said enzyme causing transformation of the region from an unmodified to a modified state; and
      (b) a detection region, which is not modified by the enzyme and can be bound by a reporter molecule irrespective of the state of modification of the enzyme modifiable region,
   (ii) a selective capture zone to receive the test sample, wherein the selective capture zone comprises selective recognition molecules capable of binding to the enzyme modifiable region of the indicator molecule selectively in one or other of the modified or unmodified states; and
   (iii) a detection zone to receive the test sample following contact of the test sample with the selective capture zone, wherein the detection zone is spatially separated from the selective capture zone such that exposure of the test sample to the detection zone occurs after prior exposure of the test sample to the selective capture zone and wherein only indicator molecules that do not bind to the selective recognition molecules in the selective capture zone pass into the detection zone and wherein the indicator molecule is detected at the selective capture zone and/or the detection zone; and wherein the device additionally comprises a reporter molecule bound or capable of binding directly to the detection region of the indicator molecule, and the binding of the reporter molecule to the indicator molecule occurs irrespective of the state of modification of the enzyme modifiable region.

2. The device of claim 1 wherein the detection region of the indicator molecule comprises a capture site and the detection zone comprises capture molecules capable of specifically binding to the capture site of the indicator molecule if said indicator molecule is present.

3. The device of claim 1 wherein the enzyme modifiable region of the indicator molecule comprises a peptide, a protein, a carbohydrate, a lipid or a nucleic acid.

4. The device of claim 1 wherein the enzyme to be detected is selected from the group consisting of oxidoreductases, transferases, hydrolases, lyases, isomerases and ligases, including the subcategories of protease; peptidase; lipase; nuclease; carbohydrase; phosphatase; sulphatase; neuraminidase; esterase; DNAse; RNAse; kinase; glycosyl transferase; oxidase; reductase; and transaminase.

5. The device of claim 1 wherein the enzyme to be detected is a matrix metalloprotease or human neutrophil-derived elastase.

6. The device of claim 1 wherein the selective recognition molecule is an antibody or antigen binding fragment thereof, avidin, streptavidin or a derivative thereof, a lectin, a nucleic acid molecule, a receptor molecule, or a hormone binding protein.

7. The device of claim 1 wherein the enzyme modifiable region cannot be modified by the enzyme once the indicator molecule is bound by a selective recognition molecule.

8. The device of claim 2 wherein the capture site and capture molecule are two halves of a binding pair selected from the group consisting of an antigen and an antibody or antigen binding fragment thereof; biotin and avidin, streptavidin, neutravidin or captavidin; an immunoglobulin or appropriate domain thereof and protein A or G; a carbohydrate and a lectin; complementary nucleotide sequences; a ligand and a receptor molecule; a hormone and hormone binding protein; an enzyme cofactor and an enzyme; an enzyme inhibitor and an enzyme; a cellulose binding domain and cellulose fibres; immobilised aminophenyl boronic acid and cis-diol bearing molecules; and xyloglucan and cellulose fibres and analogues, derivatives and fragments thereof.

9. The device of claim 1 wherein the detection region of the indicator molecule comprises a detection site, distinct and spatially separated from the capture site, and the reporter molecule(s) bind(s) to the detection region via the detection site.

10. The device of claim 1 wherein the reporter molecule binds to the detection region via the capture site, wherein binding of the reporter molecule to the capture site does not impair the ability of the capture site to bind capture molecules.

11. The device of claim 1 wherein binding of the reporter molecule to the detection region is indirect and mediated by an adaptor capable of simultaneously binding the detection region and the reporter molecule.

12. The device of claim 1 wherein multiple reporter molecules may bind to each indicator molecule.

13. The device of claim 11 wherein the adaptor binds to the capture site within the detection region of the indicator molecule such that the capture site binds indirectly to the capture molecule present in the detection zone of the device via the adaptor.

14. The device of claim 1 wherein the detection zone comprises a solid phase support and the capture molecule is located on or within said solid phase support.

15. The device of claim 1 wherein the device is a flow device, and the selective capture zone and detection zone are present at sequential locations along a chromatographic medium.

16. The device of claim 1 wherein the detection zone additionally comprises an immobilised recognition molecule to which the reporter molecule binds in the absence of indicator molecule.

\* \* \* \* \*

SEQUENCE LISTING

```
<160> NUMBER OF SEQ ID NOS: 1

<210> SEQ ID NO 1
<211> LENGTH: 8
<212> TYPE: PRT
<213> ORGANISM: Artificial sequence
<220> FEATURE:
<223> OTHER INFORMATION: Synthetic peptide

<400> SEQUENCE: 1

Gly Pro Gln Gly Ile Phe Gly Gln
1               5
```